( 12 ) United States Patent
Hatakeyama

(10) Patent No.: US 11,530,312 B2
(45) Date of Patent: Dec. 20, 2022

(54) STRETCHABLE WIRING FILM AND METHOD FOR FORMING THE SAME

(71) Applicant: SHIN-ETSU CHEMICAL CO., LTD., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 235 days.

(21) Appl. No.: 16/707,208

(22) Filed: Dec. 9, 2019

(65) Prior Publication Data

US 2020/0207952 A1    Jul. 2, 2020

(30) Foreign Application Priority Data

Dec. 26, 2018  (JP) .............................. JP2018-243484

(51) Int. Cl.
  *C08K 7/10*      (2006.01)
  *C08L 21/00*     (2006.01)
  (Continued)

(52) U.S. Cl.
  CPC ............ *C08K 7/10* (2013.01); *C08F 290/067* (2013.01); *C08G 18/3893* (2013.01); *C08G 18/4238* (2013.01); *C08G 18/61* (2013.01); *C08G 18/755* (2013.01); *C08J 5/18* (2013.01); *C08L 21/00* (2013.01); *C09J 9/02* (2013.01); *H01B 1/22* (2013.01); *H01B 1/24* (2013.01); *H01B 5/14* (2013.01); *H01B 5/16* (2013.01);
  (Continued)

(58) Field of Classification Search
  None
  See application file for complete search history.

(56) References Cited

U.S. PATENT DOCUMENTS

2004/0192082 A1  9/2004 Wagner et al.
2014/0218872 A1  8/2014 Park et al.
(Continued)

FOREIGN PATENT DOCUMENTS

CN    103813896 A    5/2014
JP    2001-018329 A  1/2001
(Continued)

OTHER PUBLICATIONS

Dec. 9, 2019 U.S. Appl. No. 16/707,161 in the name of Jun Hatakeyama.
(Continued)

*Primary Examiner* — Katie L. Hammer
(74) *Attorney, Agent, or Firm* — Oliff PLC

(57) ABSTRACT

A stretchable wiring film includes: (A) a stretchable film made of, at least as a top surface of the stretchable film, a cured product of a stretchable film material containing a silicone polyurethane resin; and (B) a stretchable wiring. The top surface of the stretchable film has a repeated uneven pattern formed with depths of 0.1 μm to 5 mm and pitches of 0.1 μm to 10 mm. The stretchable wiring is formed on the top surface of the stretchable film where the repeated uneven pattern is formed. Thus, the present invention provides: a stretchable wiring film having less decrease in electric conductivity in stretching and excellent water repellency on the film top surface; and a method for forming the stretchable wiring film.

16 Claims, 7 Drawing Sheets

(a)

6

(b)

6

(51) Int. Cl.
    *C09J 9/02* (2006.01)
    *H01B 1/22* (2006.01)
    *H01B 5/16* (2006.01)
    *C08F 290/06* (2006.01)
    *C08G 18/42* (2006.01)
    *C08G 18/75* (2006.01)
    *C08G 18/61* (2006.01)
    *C08J 5/18* (2006.01)
    *H01B 1/24* (2006.01)
    *H05K 1/09* (2006.01)
    *C08G 18/38* (2006.01)
    *H01B 5/14* (2006.01)
    *H05K 3/12* (2006.01)
    *H05K 1/02* (2006.01)

(52) U.S. Cl.
    CPC .......... *H05K 1/0283* (2013.01); *H05K 1/09* (2013.01); *H05K 1/095* (2013.01); *H05K 3/12* (2013.01); *C08J 2375/04* (2013.01)

(56) References Cited

U.S. PATENT DOCUMENTS

| | | |
|---|---|---|
| 2014/0220306 A1 | 8/2014 | Uchida et al. |
| 2015/0140884 A1 | 5/2015 | Mizuma et al. |
| 2016/0052227 A1 | 2/2016 | Takihara et al. |
| 2017/0335076 A1 | 11/2017 | Hatakeyama et al. |
| 2018/0134860 A1 | 5/2018 | Hatakeyama et al. |
| 2018/0215876 A1 | 8/2018 | Hatakeyama et al. |
| 2019/0106528 A1 | 4/2019 | Hatakeyama et al. |
| 2019/0112413 A1 | 4/2019 | Hatakeyama et al. |
| 2019/0233645 A1 | 8/2019 | Hatakeyama et al. |
| 2019/0241709 A1 | 8/2019 | Hatakeyama et al. |
| 2020/0267835 A1* | 8/2020 | Okimoto .................. H01B 7/08 |

FOREIGN PATENT DOCUMENTS

| | | |
|---|---|---|
| JP | 2004-033468 A | 2/2004 |
| JP | 2012-152725 A | 8/2012 |
| JP | 2013-256727 A | 12/2013 |
| JP | 2015-157875 A | 9/2015 |
| JP | 2018-083935 A | 5/2018 |
| JP | 6343903 B2 | 6/2018 |
| JP | 2018-123304 A | 8/2018 |
| KR | 10-2010-0018006 A | 2/2010 |
| KR | 10-2018-0134278 A | 12/2018 |
| TW | 201809039 A | 3/2018 |
| TW | 201829563 A | 8/2018 |
| WO | 2016/204162 A1 | 12/2016 |
| WO | 2017/217509 A1 | 12/2017 |
| WO | 2018/110632 A1 | 6/2018 |

OTHER PUBLICATIONS

Sep. 1, 2021 Office Action issued in Korean Patent Application No. 10-2019-0173234.
Jul. 21, 2021 Office Action issued in Chinese Patent Application No. 201911356778.5.
Apr. 15, 2021 Office Action issued in Korean Patent Application No. 10-2019-0173233.
May 6, 2020 Extended European Search Report issued in European Patent Application No. 19217763.2.
May 6, 2020 Extended European Search Report issued in European Patent Application No. 19217759.0.
May 3, 2022 Office Action Issued in U.S. Appl. No. 16/707,161.
Aug. 11, 2022 Notice of Allowance issued in U.S. Appl. No. 16/707,161.
Sep. 27, 2022 Office Action issued in Japanese Patent Application No. 2019-184092.
Aug. 23, 2022 Office Action issued in Japanese Patent Application No. 2019-184070.

* cited by examiner

[FIG. 1]
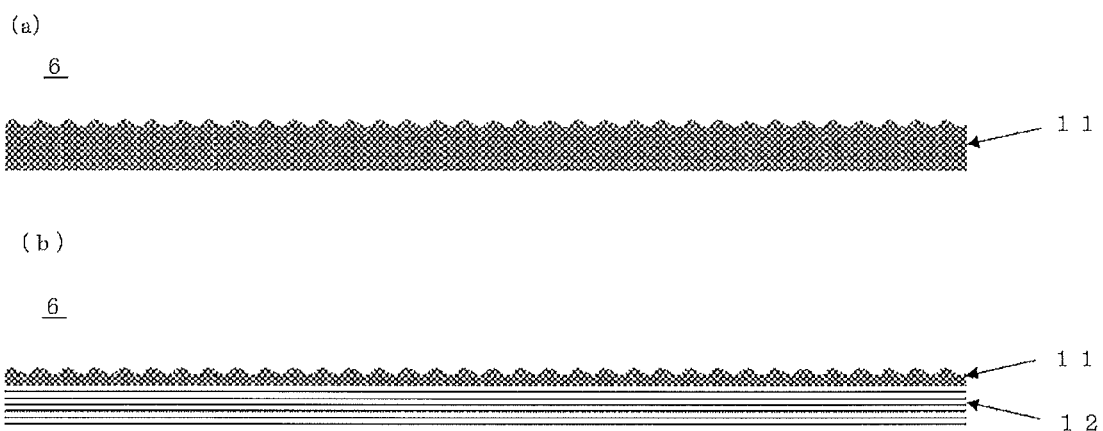
[FIG. 2]
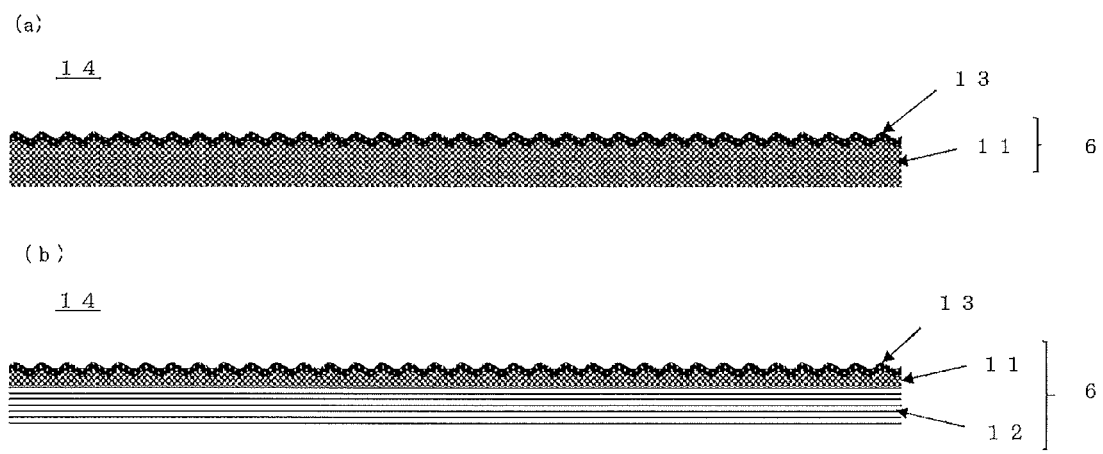

[FIG. 3]
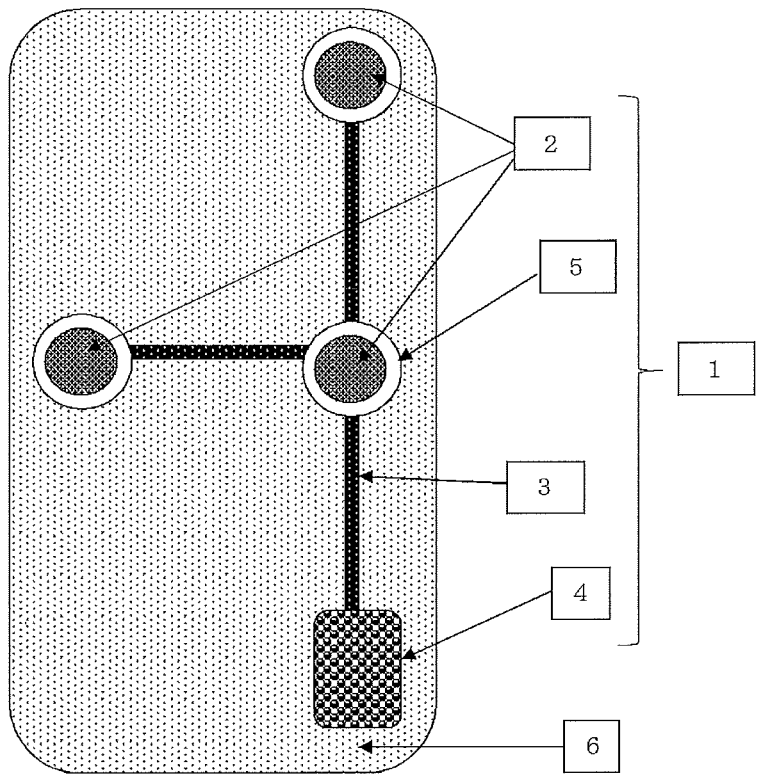
[FIG. 4]
(a)
(b)
(c)
(d)
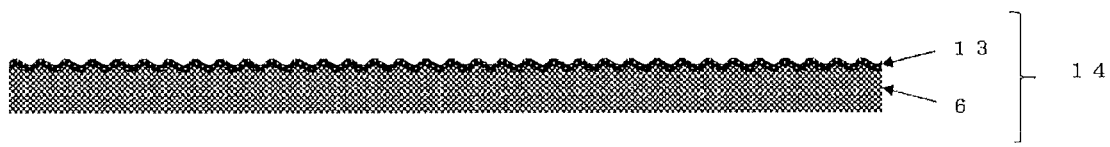

[FIG. 5]
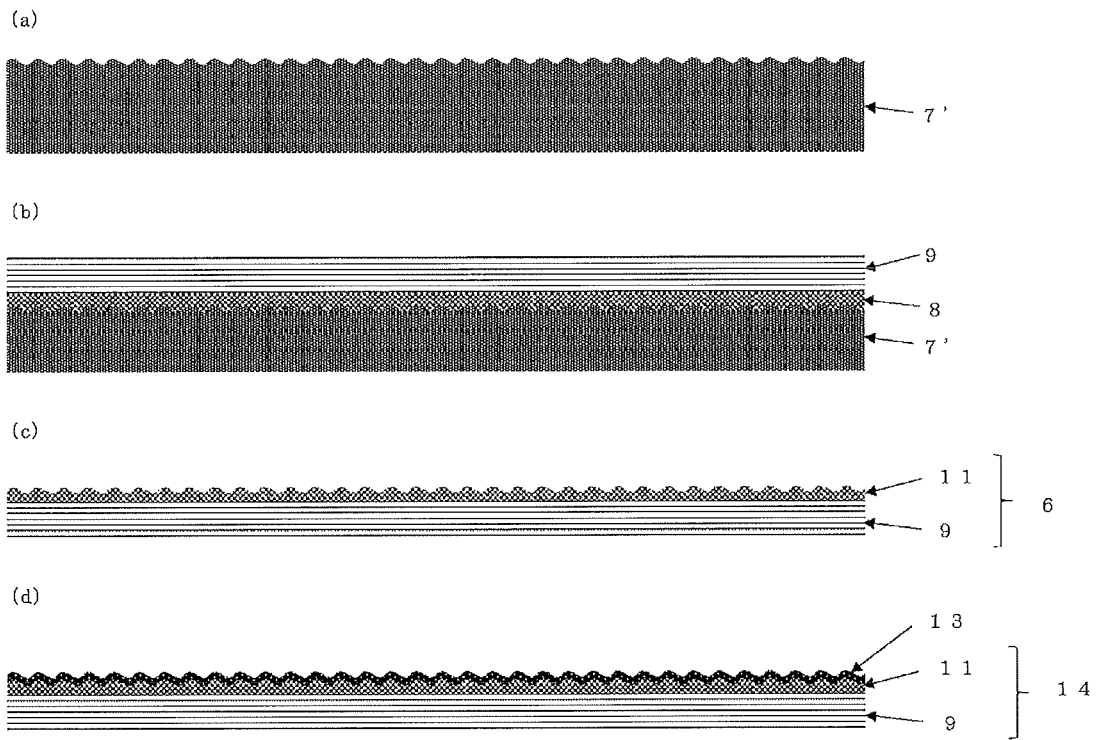
[FIG. 6]
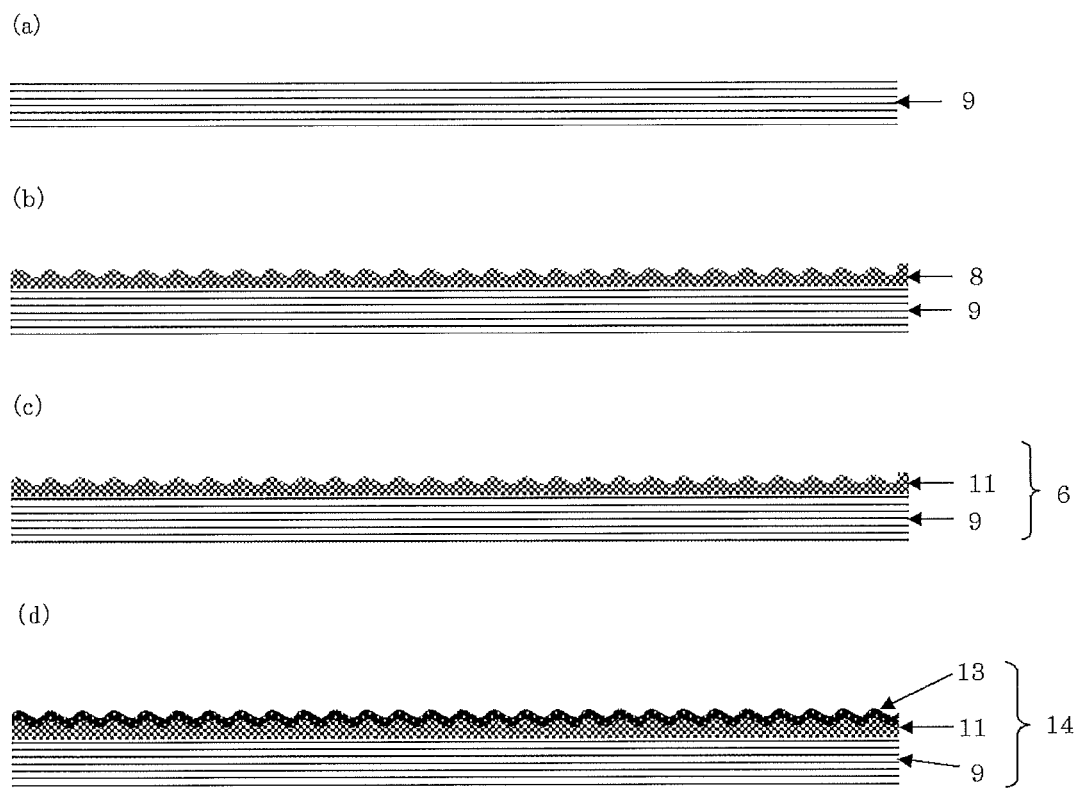

[FIG. 7]
(a)
(b)
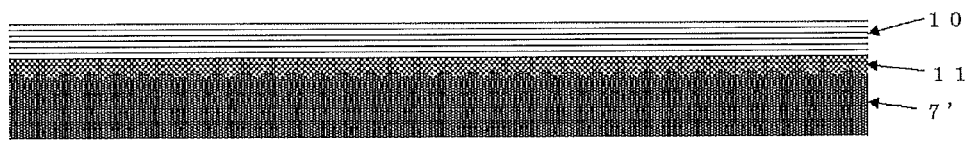
(c)
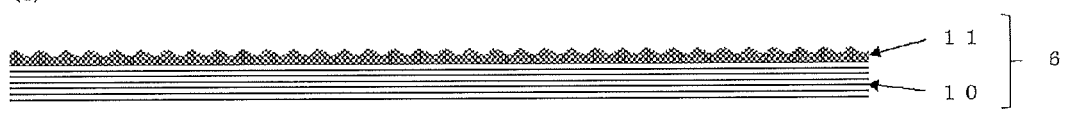
(d)
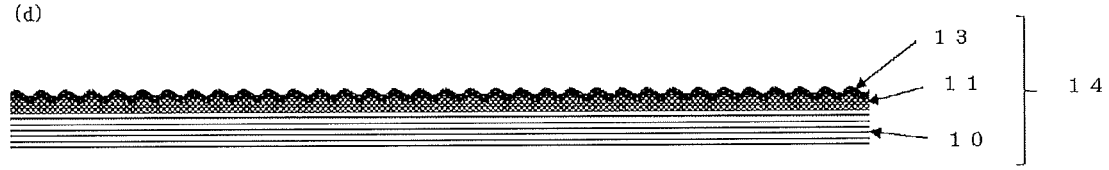

[FIG. 8]
(e)
(f)
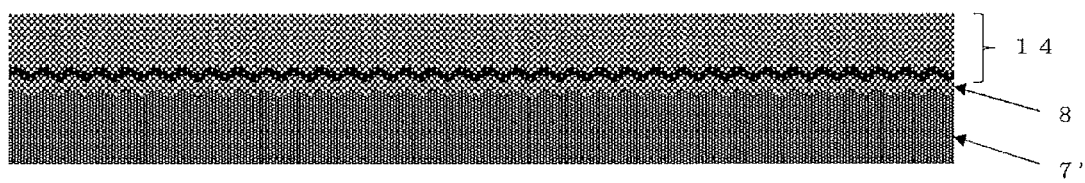
(g)
(h)
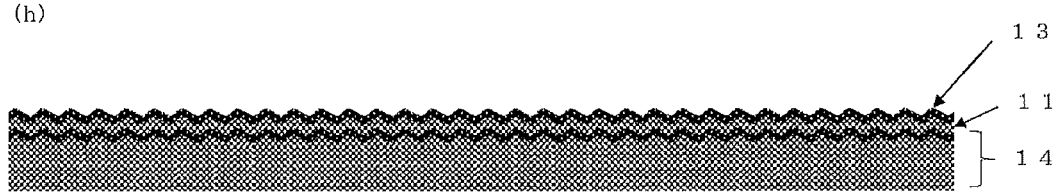
(i)
[FIG. 9]
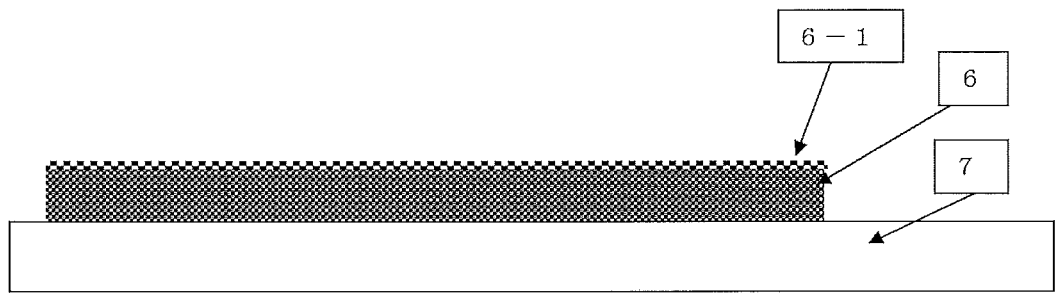

[FIG. 10]
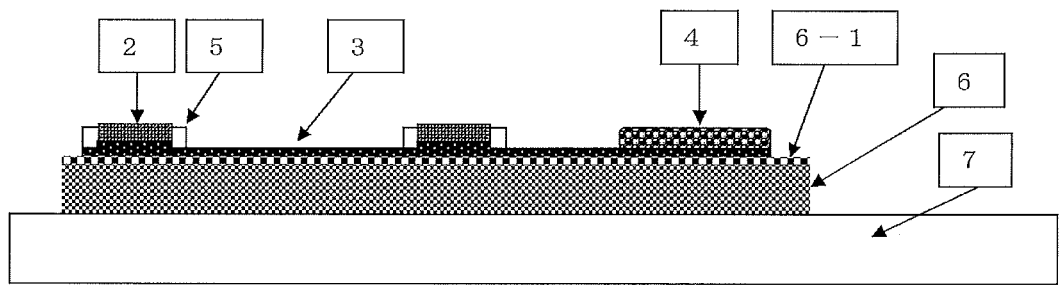
[FIG. 11]
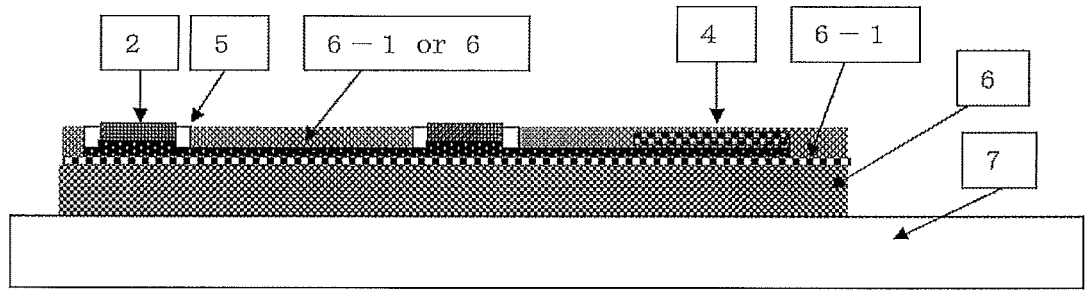
[FIG. 12]
[FIG. 13]
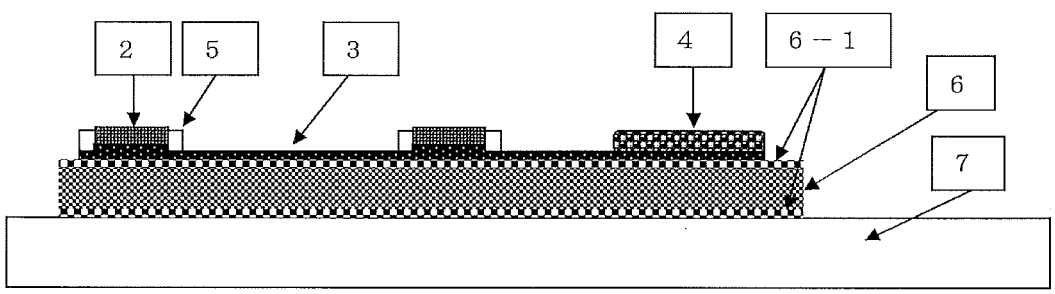

[FIG. 14]
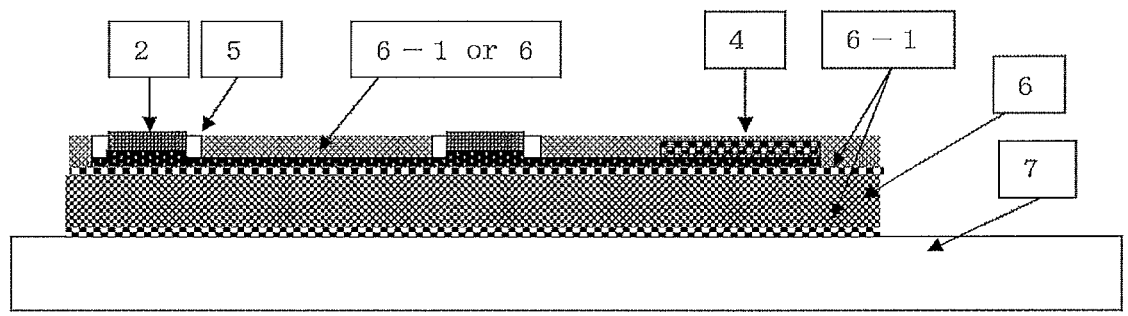

STRETCHABLE WIRING FILM AND METHOD FOR FORMING THE SAME

TECHNICAL FIELD

The present invention relates to: a stretchable wiring film which has high stretchability, high strength, and high water repellency, as well as less decrease in electric conductivity when the stretchable wiring film is stretched; and a method for forming the stretchable wiring film.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

One typical wearable device is attached to the body of a user to constantly monitor the state of physical conditions. The wearable device normally includes a bio-electrode for detecting an electric signal transmitted from a body, wires for sending the electric signal to a sensor, a semiconductor chip serving as a sensor, and a battery, as well as an adhesive pad to be attached to the skin. Patent Document 1 describes detailed structures of a bio-electrode, a wiring part surrounding the bio-electrode, and an adhesive pad. The wearable device disclosed in Patent Document 1 includes a bio-electrode, a silicone-based adhesive film disposed around the bio-electrode, a sensor device, and a meandering-shaped stretchable silver wiring part coated with a stretchable urethane film between the bio-electrode and the sensor device, which are connected by the wiring part. Even if such a metal wire does not have stretchability by itself, the electric conductivity of the metal wire to be stretched can be secured by forming the wire in such a meandering shape that horseshoes are aligned, or by preparing a wrinkled substrate.

If a wire not in a meandering shape but in a straight shape is electrically conductive when stretched also, the wire area is more compact and the design will be more attractive. Hence, stretchable electro-conductive pastes and electrically conductive inks have been actively developed. Examples thereof include stretchable wirings using galinstan consisting of gallium-indium-tin or a liquid metal consisting of gallium-indium, an electro-conductive paste containing silicone mixed with silver particles (Patent Document 2), a mixture of a polyester resin and/or a polyurethane resin with metal particles (Patent Document 3), a mixture containing silver nanowires as a metal additive (Patent Document 4), a stretchable wiring containing a fluorine rubber, a surfactant, and a silver filler in combination in which silver nanoparticles are generated during annealing (Patent Document 5), and the like. Like these, there have been many proposals and applications most of which are electro-conductive pastes obtained by mixing stretchable resins with metal fillers such as silver.

An electro-conductive wire using an electro-conductive paste in which a resin is mixed with a metal filler is electrically conductive by electron percolation phenomenon among the electro-conductive particles. The electric conductivity of such an electro-conductive wire is decreased when the applied wire is stretched together with a substrate. When the wire is stretched, the distances of the metal particles in the wire are increased, thereby increasing the insulation distance. As a result, the percolation phenomenon hardly occurs, so that the electric conductivity is decreased.

Stretchable substrates for mounting stretchable wirings have also been developed. As the stretchable substrates, cloths using stretchable fibers and stretchable sheets have been examined. Examples of the stretchable sheets include silicone sheets and urethane sheets.

A urethane film has high stretchability and strength, and excellent mechanical properties as a film coated on a stretchable substrate or a stretchable wiring. Unfortunately, the hydrolysis inherent in the urethane film lowers its stretchability and strength. Meanwhile, the silicone film has no such hydrolytic nature, but the strength inherently remains low.

Hence, the use of silicone urethane polymers, whose main chain has both a urethane bond and a siloxane bond, has been examined. Advantageously, cured products of the silicone urethane polymer are characterized by higher strength than single silicone and less hydrolytic nature than single polyurethane. Such cured products unfortunately fail to achieve the strength equivalent to single polyurethane and the water repellency equivalent to single silicone, and the strength and water repellency are in-betweens of those inherent in silicone and polyurethane.

Highly stretchable urethane films tend to have a sticky top surface to the touch. The sticky top surface causes difficulty in separating films that are put together, and failure in printing since the film is stuck to a printing plate when screen printing is performed on this film. On the other hand, silicone films have high release characteristics and are prevented from sticking with each other thereby. However, due to the lower strength of silicone, thin silicone films easily break in stretching. When screen printing is performed on a silicone film, failure in printing due to sticking with a printing plate can be avoided, but the lower adhesion to paste causes peeling off of the cured paste. This comes from high release characteristics of a silicone top surface. On the other hand, urethane films have higher adhesion to paste and are prevented from peeling off of the cured paste.

Accordingly, it is desirable to develop a stretchable film which has higher stretchability, strength, and water repellency, and which enables printing of a stretchable electro-conductive paste on the stretchable film without peeling off of the printed paste.

CITATION LIST

Patent Literature

Patent Document 1: Japanese Patent Laid-Open Publication No. 2004-033468
Patent Document 2: WO2016/204162
Patent Document 3: Japanese Patent No. 6343903
Patent Document 4: WO2017/217509 A1
Patent Document 5: WO2018/110632 A1

SUMMARY OF INVENTION

Technical Problem

Due to these backgrounds, it has been demanded to develop: an electro-conductive paste, a printing pattern, a printing method, and a stretchable substrate which prevent the electric conductivity from decreasing in stretching.

In view of the circumstances, the present invention aims to provide: a stretchable wiring film having less decrease in electric conductivity in stretching and excellent water repellency on the film top surface; and a method for forming the stretchable wiring film.

Solution to Problem

To achieve the object, the present invention provides a stretchable wiring film comprising:

(A) a stretchable film comprising, at least as a top surface of the stretchable film, a cured product of a stretchable film material comprising a silicone polyurethane resin, wherein the top surface of the stretchable film has a repeated uneven pattern formed with depths of 0.1 μm to 5 mm and pitches of 0.1 μm to 10 mm; and (B) a stretchable wiring, wherein the stretchable wiring is formed on the top surface of the stretchable film where the repeated uneven pattern is formed.

Such a stretchable wiring film has less decrease in electric conductivity in stretching and has excellent water repellency on the film top surface.

The stretchable wiring preferably contains an electro-conductive powder made of carbon or a metal selected from gold, silver, platinum, copper, tin, titanium, nickel, aluminum, tungsten, molybdenum, ruthenium, chromium, and indium.

In the inventive stretchable wiring film, such a stretchable wiring is favorably used.

Moreover, the silicone polyurethane resin is preferably a silicone-pendant type polyurethane resin having a structure shown by the following general formula (1):

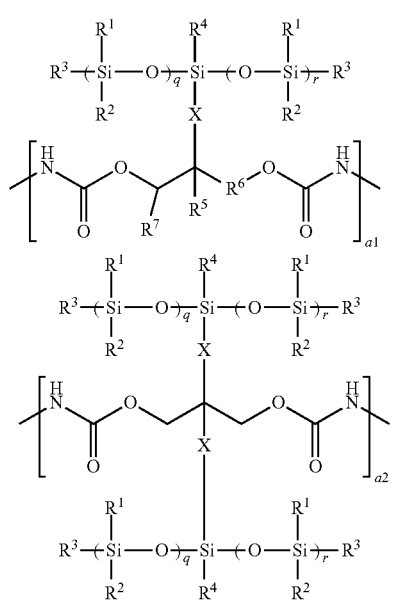

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a —(OSiR$^1$R$^2$)$_s$—OSiR$^1$R$^2$R$^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2≤1.0.

Such a silicone polyurethane resin enables the stretchable wiring film with more excellent strength.

Further, the silicone-pendant type polyurethane resin preferably has a structure shown by the following general formula (2):

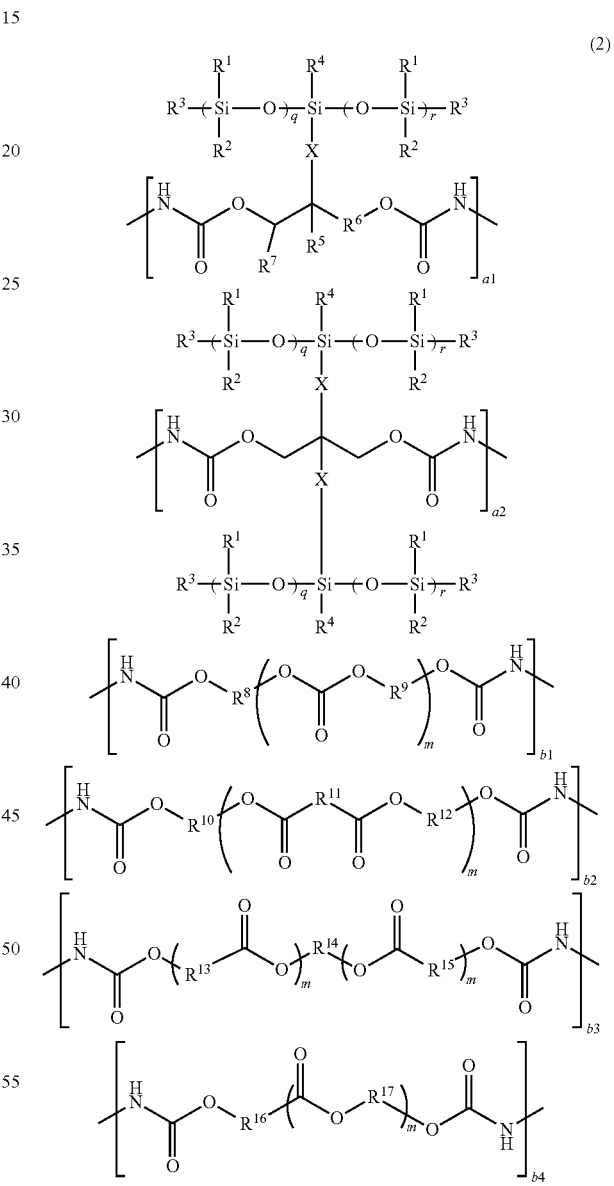

wherein $R^1$ to $R^7$, X, "q", "r", a1, and a2 are as defined above; $R^8$ to $R^{17}$ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of 0≤b1<1.0, 0≤b2<1.0, 0≤b3<1.0, 0≤b4<1.0, and 0<b1+b2+b3+b4<1.0.

Such a silicone-pendant type polyurethane resin makes the stretchable wiring film have further improved strength and the film top surface cause less sticking.

Furthermore, the silicone-pendant type polyurethane resin preferably has a structure shown by the following general formula (3):

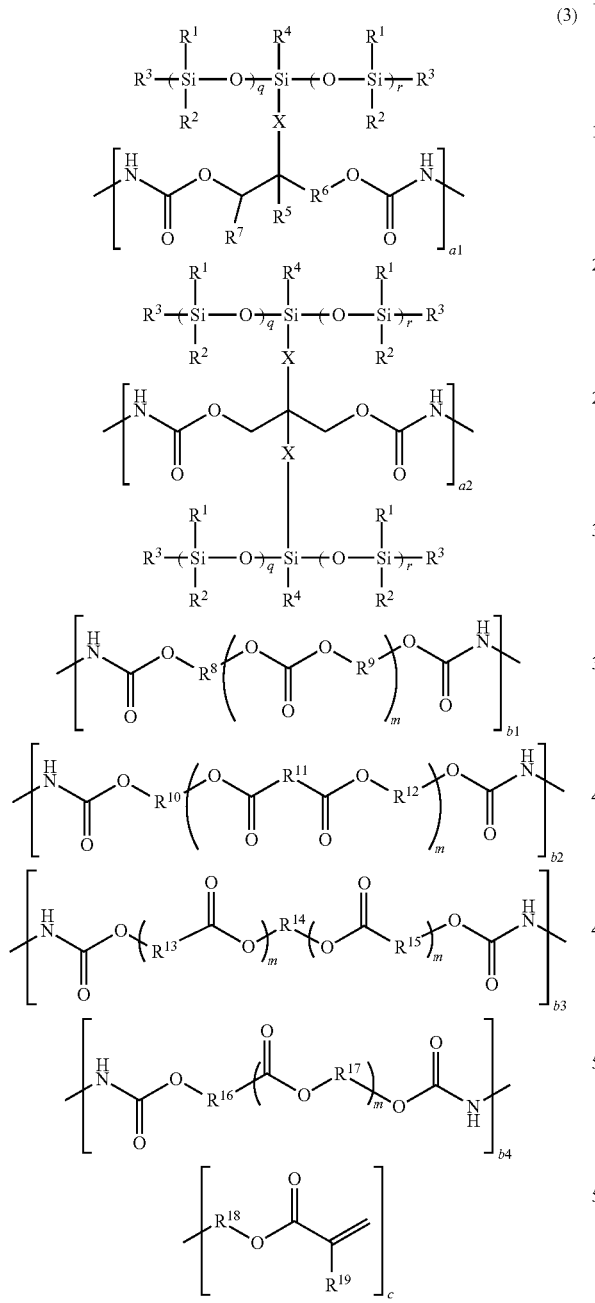

wherein $R^1$ to $R^{17}$, X, "m", "q", "r", a1, a2, b1, b2, b3, and b4 are as defined above; $R^{18}$ represents a linear, branched, or cyclic alkylene group having 1 to 20 carbon atoms and optionally having an ether group or an ester group; $R^{19}$ represents a hydrogen atom or a methyl group; and "c" represents the number of unit in one molecule and satisfies a range of 1≤c≤4.

Such a silicone-pendant type polyurethane resin is particularly suitably cured by heating and/or light irradiation.

The stretchable wiring film preferably has an elongation percentage in a range of 5 to 500%.

Such a stretchable wiring film can be favorably used for a bio-electrode, for example.

The stretchable wiring film preferably comprises a stretchable film configured to cover a stretchable wiring.

The inventive stretchable wiring film may have such a configuration.

The stretchable film configured to cover a stretchable wiring is preferably a cured product of a stretchable film material comprising the silicone-pendant type polyurethane resin having a structure shown by the general formula (1).

In such a stretchable wiring film, the stretchable wiring is covered with the stretchable film having higher strength.

The present invention also provides a method for forming a stretchable wiring film, comprising the steps of:

(1) applying a stretchable film material comprising a silicone-pendant type polyurethane resin having a structure shown by the following general formula (1) onto a substrate having a repeated uneven pattern formed with depths of 0.1 μm to 5 mm and pitches of 0.1 μm to 10 mm;

(2) curing the stretchable film material by heating and/or light irradiation;

(3) peeling a cured product of the stretchable film material from the substrate to form a stretchable film having a top surface with the repeated uneven pattern; and (4) applying a stretchable electro-conductive paste onto the top surface of the stretchable film where the repeated uneven pattern is formed to form a stretchable wiring,

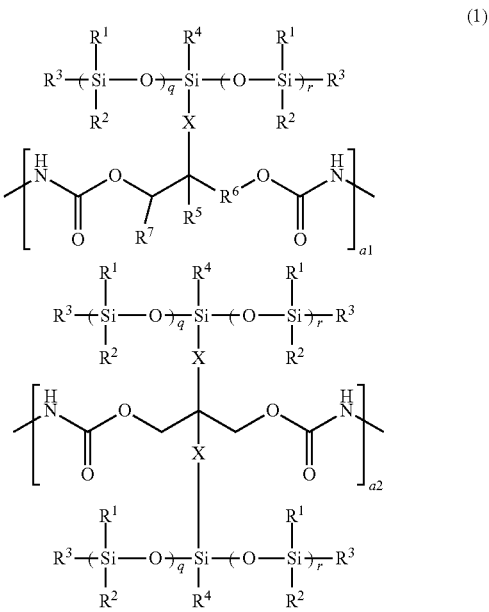

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a —(OSiR$^1$R$^2$)$_s$—OSiR$^1$R$^2$R$^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of $0 \leq a1 < 1.0$, $0 \leq a2 < 1.0$, and $0 < a1+a2 \leq 1.0$.

Such a method for forming a stretchable wiring film makes it possible to easily form a stretchable wiring film which has less decrease in electric conductivity in stretching and excellent water repellency on the film top surface.

In this event, the inventive method may comprise, between the step (1) and the step (2), (1') a step of pressure-bonding a polyurethane film onto the stretchable film material.

Alternatively, the inventive method may comprise, between the step (2) and the step (3), (2'-1) a step of coating the cured product of the stretchable film material with a stretchable film material containing a polyurethane resin, and (2'-2) a step of curing the stretchable film material containing the polyurethane resin by heating and/or light irradiation to form a polyurethane film.

Such methods for forming a stretchable wiring film make it possible to easily produce a stretchable wiring film including a stretchable film which is a laminate of: the top surface having the repeated uneven pattern; and the other portion having a different composition from that of the top surface.

The stretchable electro-conductive paste preferably contains an electro-conductive powder made of carbon or a metal selected from gold, silver, platinum, copper, tin, titanium, nickel, aluminum, tungsten, molybdenum, ruthenium, chromium, and indium.

The inventive method for forming a stretchable wiring film makes it possible to form a stretchable wiring film in which the stretchable wiring containing such an electro-conductive powder is formed.

Advantageous Effects of Invention

As described above, the inventive stretchable wiring film has less decrease in electric conductivity when stretched. The stretchable film on which the conductive wiring is formed has excellent stretchability and strength equivalent to those of polyurethane, and the film top surface is free from sticking when touched and super water repellent so that water drops can roll on the film top surface. Moreover, in the present invention, the presence of the unevenness on the top surface of the layer based on the silicone pendant polyurethane in the stretchable film causes super water repellent phenomenon. The inventive stretchable wiring film not only makes water droplets hardly adhere thereto but also can reduce the adhesion of foreign matters, and the top surface of the inventive stretchable wiring film is free from sticking and has favorable texture. Further, when a conductive wiring is formed on this uneven substrate, a fine meandering-shaped structure is formed in a depth direction of the film. This makes it possible to prevent the electric conductivity from decreasing in stretching. Accordingly, the inventive stretchable wiring film is particularly favorably usable as a stretchable film including a wiring part for connecting a bio-electrode to a sensor for a wearable device. Furthermore, the inventive method for forming a stretchable wiring film makes it possible to easily form a stretchable wiring film as described above.

BRIEF DESCRIPTION OF DRAWINGS

FIG. 1 is a schematic illustration showing examples of a stretchable film used in the present invention;

FIG. 2 is a schematic illustration showing examples of the inventive stretchable wiring film;

FIG. 3 is a schematic illustration of an electrocardiograph formed on the inventive stretchable wiring film, which is viewed from a bio-electrode side;

FIG. 4 illustrates an example of the inventive method for forming a stretchable wiring film;

FIG. 5 illustrates another example of the inventive method for forming a stretchable wiring film;

FIG. 6 illustrates still another example of the inventive method for forming a stretchable wiring film;

FIG. 7 illustrates still another example of the inventive method for forming a stretchable wiring film;

FIG. 8 illustrates an example of the inventive method for forming a stretchable wiring film in which multiple wires are formed and an insulator film is disposed between the wires;

FIG. 9 is a cross-sectional view showing a state where a stretchable film is formed on a substrate;

FIG. 10 is a cross-sectional view showing a state where an electrocardiograph is formed on the stretchable film;

FIG. 11 is a cross-sectional view showing a state where a wire and a center device in FIG. 10 are covered with the silicone-urethane stretchable film;

FIG. 12 is a cross-sectional view showing a state where repeated uneven patterns are formed on both surfaces of the stretchable film;

FIG. 13 is a cross-sectional view showing a state where an electrocardiograph is formed on the stretchable film in FIG. 12; and FIG. 14 is a cross-sectional view showing a state where a wire and a center device in FIG. 13 are covered with the silicone-urethane stretchable film.

DESCRIPTION OF EMBODIMENTS

When an electro-conductive paste containing a stretchable resin mixed with a metal powder such as silver flakes is used to form a straight wire on a stretchable film and then the wire is stretched, the electric conductivity is decreased. Forming a wire having a meandering-shaped structure in a horizontal direction of the film can mitigate the decrease in electric conductivity due to the stretching. However, the wire area is increased, and a compact wire cannot be formed.

To solve such problems, the inventor has arrived at an idea that when a wire is formed on a stretchable film having fine uneven top surface, the wire has a fine meandering shape in a depth direction of the film, making it possible to prevent the decrease in electric conductivity in stretching. As the stretchable film with such an uneven top surface, for example, silicone pendant polyurethane is used. Polyurethane has sufficient stretchability and strength but has such drawbacks that the water repellency is low, and that the strength and stretchability are lowered by hydrolysis. Silicone has high water repellency but a drawback of low strength. A cured product of a silicone urethane polymer having a main chain with both a urethane bond and a siloxane bond has a drawback of low strength, although the water repellency is excellent.

When silicone rubber is used to prepare a sheet having fine uneven top surface like lotus leaves, the top surface has super water repellency. Nevertheless, this sheet easily breaks by stretching. This is because the tear strength of silicone rubber is so weak that the sheet is torn from the uneven portion by applying a tensile stress to the sheet.

A polyurethane sheet has high strength, and when the sheet is prepared to have fine uneven top surface, the sheet does not break by stretching. Nevertheless, polyurethane does not have high water repellency, so that no super water repellent phenomenon occurs on the uneven top surface.

Consequently, it has been found that when a sheet having fine uneven top surface is prepared using silicone polyurethane, a stretchable film is obtained which has excellent stretchability, with the film top surface being excellent in water repellency and free from sticking. The stretchable film is particularly suitable as a stretchable film to form a stretchable wiring in a wearable device. Further, it has been found that the decrease in electric conductivity in stretching can be prevented by forming a stretchable wiring on the top surface of a stretchable film with such uneven pattern. These findings have led to the completion of the present invention.

Thus, the present invention is a stretchable wiring film comprising:

(A) a stretchable film comprising, at least as a top surface of the stretchable film, a cured product of a stretchable film material comprising a silicone polyurethane resin, wherein the top surface of the stretchable film has a repeated uneven pattern formed with depths of 0.1 μm to 5 mm and pitches of 0.1 μm to 10 mm; and (B) a stretchable wiring, wherein the stretchable wiring is formed on the top surface of the stretchable film where the repeated uneven pattern is formed.

Hereinafter, the present invention will be described in detail. However, the present invention is not limited thereto.
<Stretchable Wiring>

The material for forming a stretchable wiring of the present invention is preferably a stretchable resin mixed with an electro-conductive powder made of carbon or a metal selected from gold, silver, platinum, copper, tin, titanium, nickel, aluminum, tungsten, molybdenum, ruthenium, chromium, and indium. Among these, a silver powder is most preferably used.

Examples of the stretchable resin include resins selected from polyurethane, polyester, polyamide, polyimide, poly(meth)acrylate, styrene-butadiene rubber, fluorine rubber, and silicone. The proportion of the electro-conductive powder selected from carbon and metals contained in the resins preferably ranges from 20 to 95 mass % based on a total amount of the resin in the stretchable wiring.

The form of the electro-conductive powder selected from carbon and metals may be flake-shaped, spherical, or fibrous powder. Examples of the fibrous electro-conductive material include silver nanofibers and carbon nanotubes.

The material for forming the stretchable wiring may contain an organic solvent, too. The kind of the organic solvent will be described in the section of Method for Forming Stretchable Wiring Film. The material for forming the stretchable wiring may further contain a curing catalyst for crosslink reaction.
<Stretchable Film>

The stretchable film (A) used in the present invention is a stretchable film made of, at least as a top surface of the stretchable film, a cured product of a stretchable film material containing a silicone polyurethane resin, and the top surface of the stretchable film has a repeated uneven pattern formed with depths of 0.1 μm to 5 mm and pitches of 0.1 μm to 10 mm. Note that the repeated uneven pattern can be formed with depths of 0.1 to 100 μm and pitches of 0.1 to 100 μm.

FIG. 1 shows a schematic illustration showing an example of the stretchable film used in the present invention. As shown in FIG. 1(a), a stretchable film 6 may be such that the entire film is a cured product 11 of a stretchable film material containing a silicone polyurethane resin. In this case, the top surface formed to have the repeated uneven pattern and the other portion may be formed from different compositions or the same composition. Alternatively, as shown in FIG. 1(b), only the top surface of the stretchable film 6 may be the cured product 11 of a stretchable film material containing a silicone polyurethane resin. Meanwhile, the composition of a portion 12 other than the top surface is not particularly limited as long as the portion 12 is stretchable. Alternatively, only a top surface and a bottom surface of the stretchable film 6 may be formed from the cured product of a stretchable film material containing a silicone polyurethane resin. Note that the repeated uneven pattern may be formed not only on the top surface but also on the bottom surface.

The material for forming the top surface (surface layer) having the repeated uneven pattern formed thereon is preferably a stretchable film material containing a silicone pendant polyurethane resin with polycarbonate and/or polyester soft segments to be described later. Since this material has high hardness, the uneven portion is less likely to deform by touching, so that the super water repellency is maintained. Particularly, when constituted such that the portion other than the top surface having the repeated uneven pattern is a cured product of a stretchable film material containing a polyurethane resin containing a polyether soft segment with higher stretchability and high strength while the top surface portion having the uneven pattern is a cured product of a stretchable film material containing a silicone pendant polyurethane resin containing polycarbonate and/or polyester soft segments, an excellent stretchable film is obtained which has the highest stretchability, highest strength, and highest water repellency, and the top surface of which is free from sticking without causing mutual sticking of such stretchable films.
<Silicone Polyurethane Resin>

The silicone polyurethane resin is not particularly limited. For example, a silicone-pendant type polyurethane resin having a structure shown by the following general formula (1) is preferable:

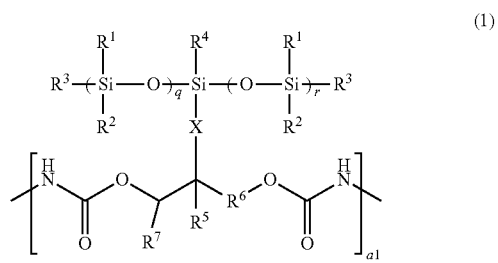

(1)

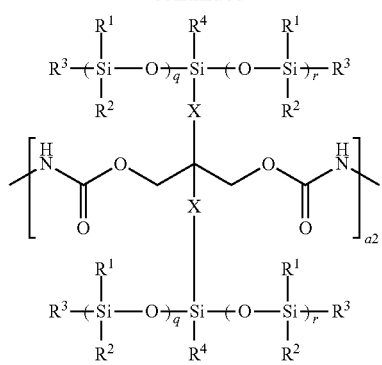

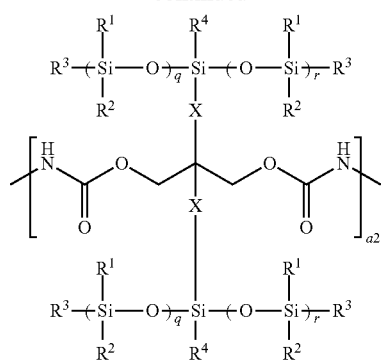

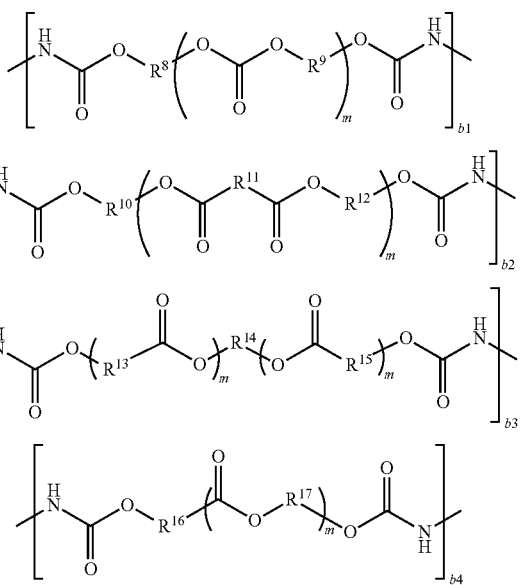

where $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a $-(OSiR^1R^2)_s-OSiR^1R^2R^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of $0 \leq a1 < 1.0$, $0 \leq a2 < 1.0$, and $0 < a1 + a2 \leq 1.0$.

The silicone pendant polyurethane has polyurethane as the main chain, and hence has high strength and high stretchability. The minimum pendant silicone chain produces high water repellent property. These enable properties of high strength, high stretchability, and high water repellency. Thus, the silicone pendant polyurethane is preferable as the silicone polyurethane resin used in the present invention.

In this case, the silicone-pendant type polyurethane resin is preferably a polycarbonate and/or polyester silicone polyurethane resin having a structure shown by the following general formula (2):

where $R^1$ to $R^7$, X, "q", "r", a1, and a2 are as defined above; $R^8$ to $R^{17}$ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of $0 \leq b1 < 1.0$, $0 \leq b2 < 1.0$, $0 \leq b3 < 1.0$, $0 \leq b4 < 1.0$, and $0 < b1 + b2 + b3 + b4 < 1.0$.

Further, in this case, the polycarbonate and/or polyester silicone polyurethane resin preferably has a structure shown by the following general formula (3), including (meth)acrylate:

(2)

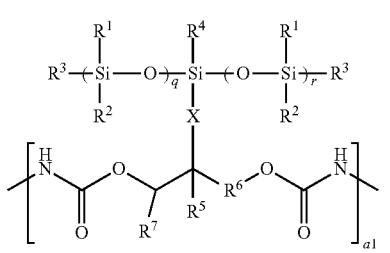

(3)

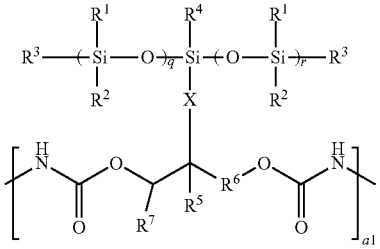

-continued

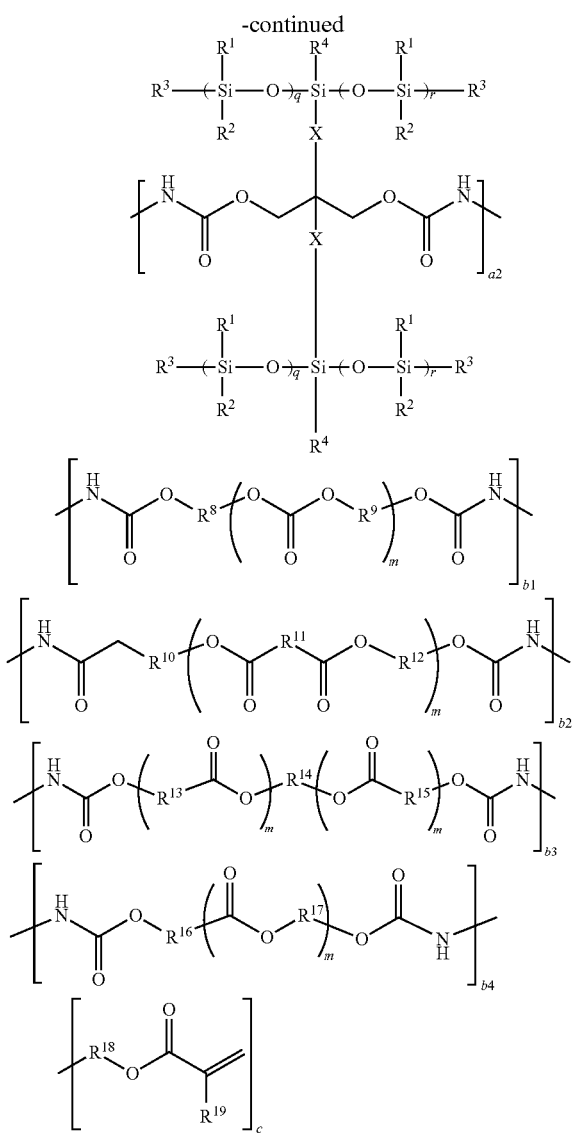

where $R^1$ to $R^{17}$, X, "m", "q", "r", a1, a2, b1, b2, b3, and b4 are as defined above; $R^{18}$ represents a linear, branched, or cyclic alkylene group having 1 to 20 carbon atoms and optionally having an ether group or an ester group; $R^{19}$ represents a hydrogen atom or a methyl group; and "c" represents the number of unit in one molecule and satisfies a range of $1 \le c \le 4$.

To the silicone polyurethane resin used in the present invention, a soft segment can be introduced. When polyether is used as a soft segment, the silicone polyurethane resin has higher stretchability, higher strength, and higher water repellency, while the film top surface is more likely to deform and stickier to the touch. When polycarbonate or polyester is used as a soft segment as described above, the high water repellency of the silicone polyurethane resin does not change, and the stretchability is lower than that when polyether is used. However, the strength is improved, high hardness is achieved, and the film top surface hardly deforms and is less sticky. Additionally, a polyester soft segment brings high water repellency, and the resulting mechanical property is intermediate between those of polyether and polycarbonate.

Examples of a diol compound for forming the structure (repeating unit) shown by a1 in the general formula (1) include a compound shown by the following general formula (a)-1'.

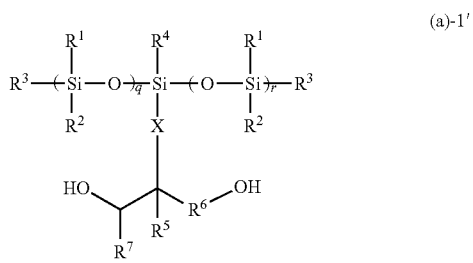

(a)-1'

$R^1$, $R^2$, and $R^3$ are as defined above, and may be identical to or different from each other. Preferable examples thereof include a methyl group, an ethyl group, an n-propyl group, an isopropyl group, an n-butyl group, an isobutyl group, a tert-butyl group, an n-pentyl group, a cyclopentyl group, an n-hexyl group, a cyclohexyl group, a phenyl group, and a 3,3,3-trifluoropropyl group. $R^4$ to $R^7$, X, "q", and "r" are as defined above.

The diol compound having a short chain silicone pendant shown by the general formula (a)-1' can be obtained, for example, by reaction of glycerin monoallyl ether and a short-chain siloxane compound having a SiH group under a platinum catalyst. Specific examples of the diol compound include the following.

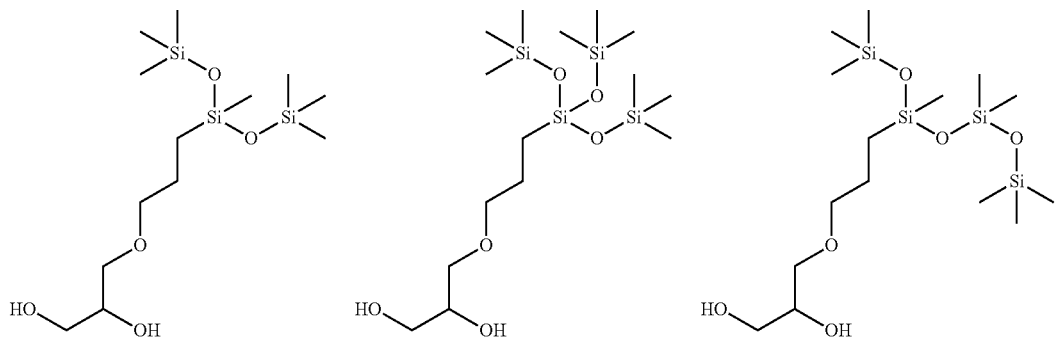

-continued
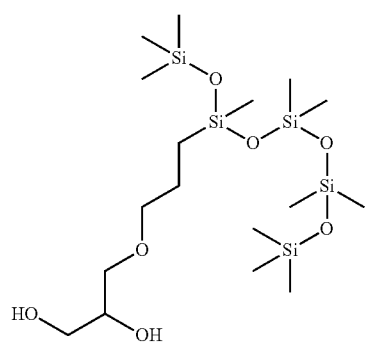
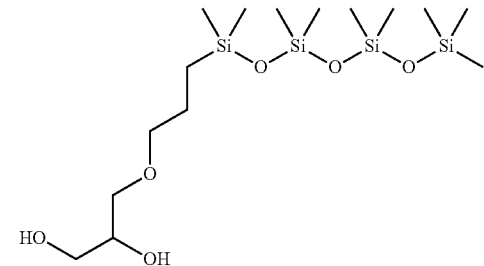
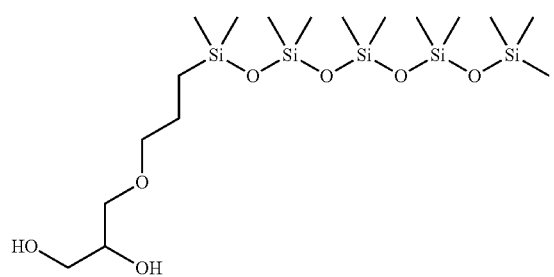
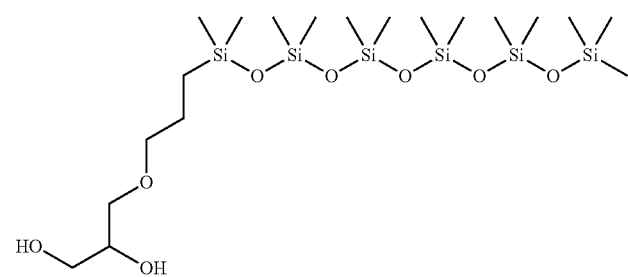
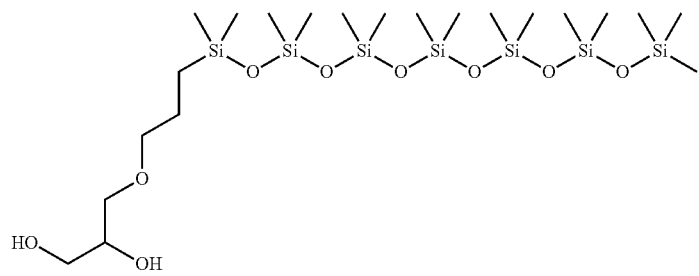
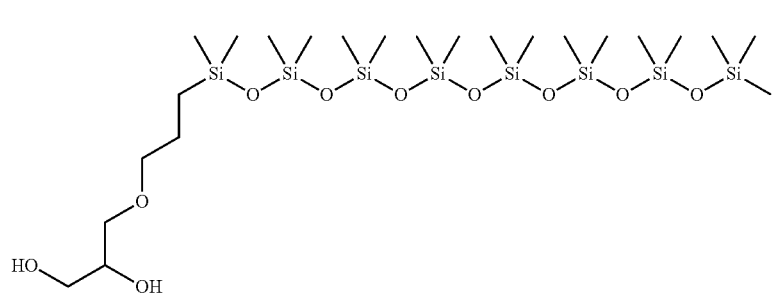
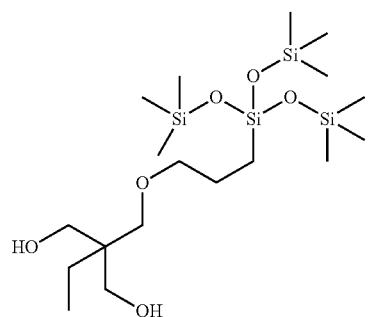
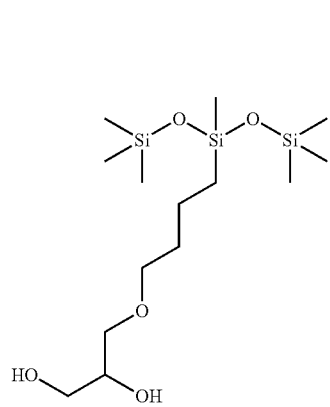
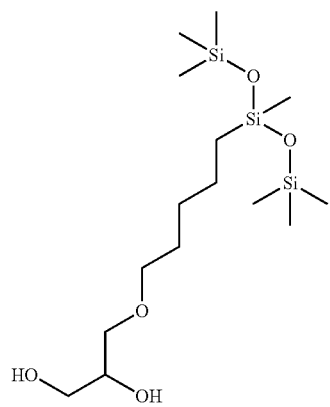
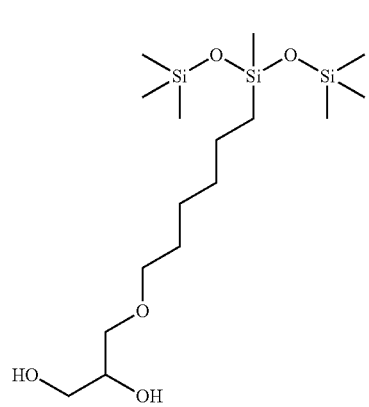

17                                                                 18
-continued
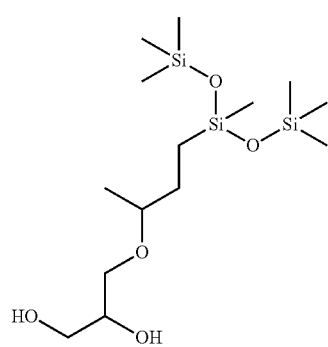 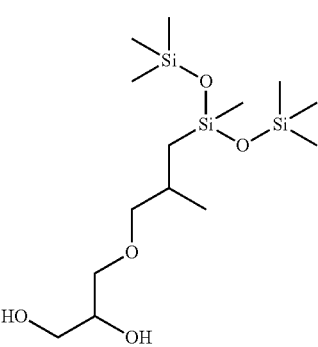
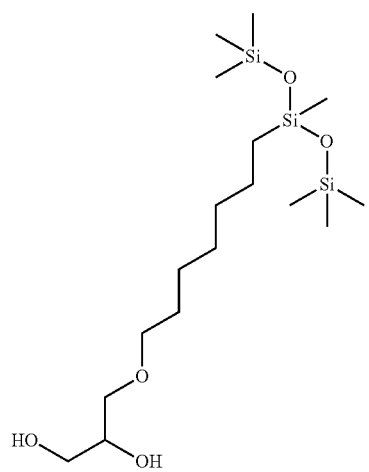 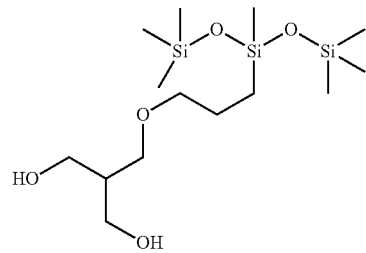 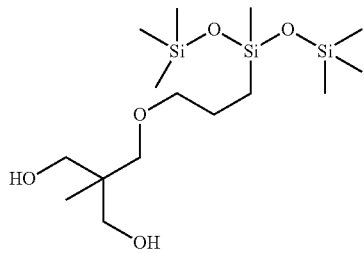
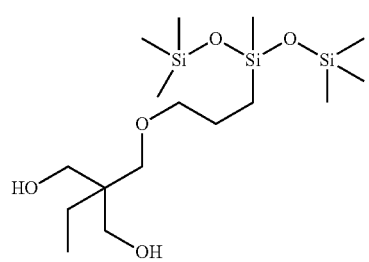 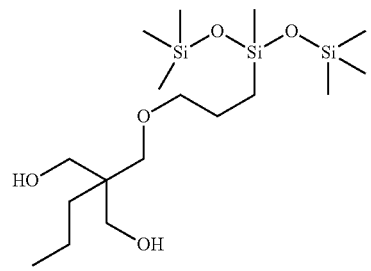 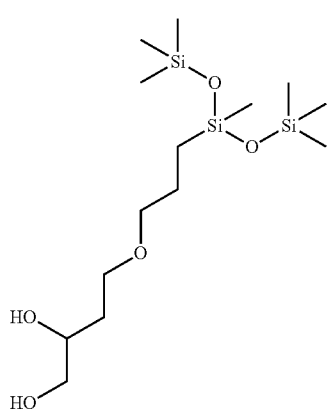
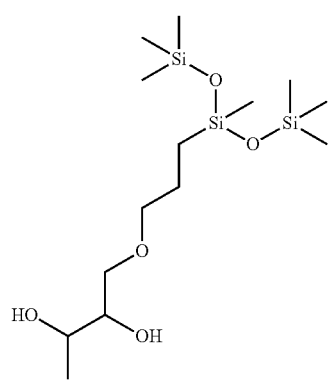 [SMILES: CC(O)C(O)COCCC[Si](C)(O[Si](C)(C)C)O[Si](C)(C)C]

Examples of a diol compound for forming the structure (repeating unit) shown by a2 in the general formula (1) include a compound shown by the following general formula (a)-2':

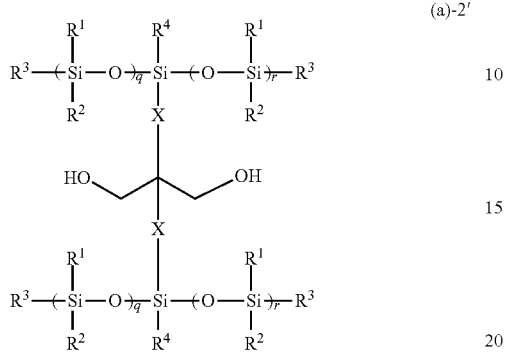

(a)-2' where $R^1$ to $R^4$, X, "q", and "r" are as defined above.

The diol compound having short chain silicone pendants shown by the general formula (a)-2' can be obtained, for example, by reaction of a dihydroxy dialkenyl compound and a short-chain siloxane compound having a SiH group under a platinum catalyst. Specific examples of the diol compound include the following.

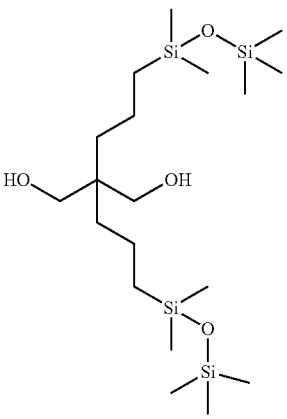

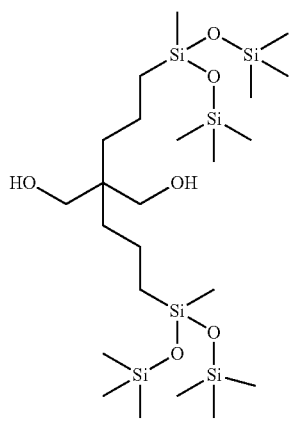

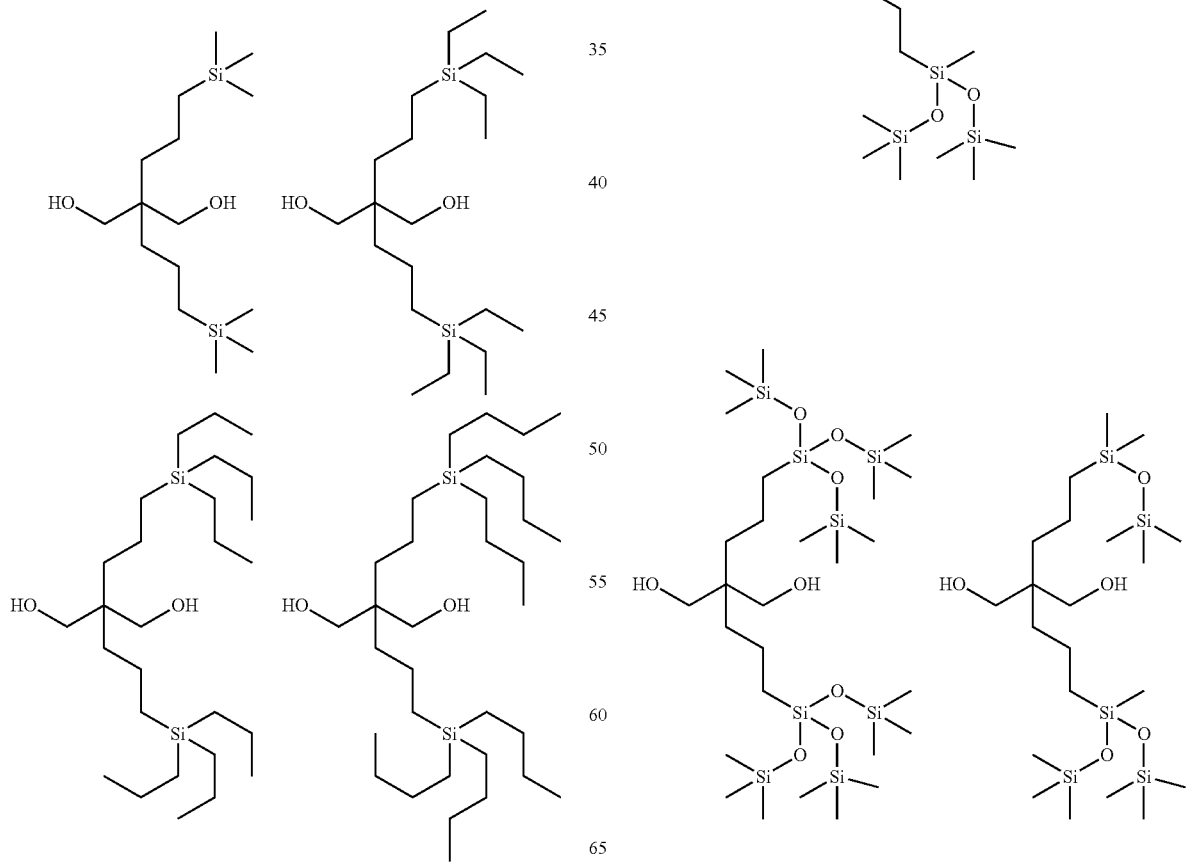

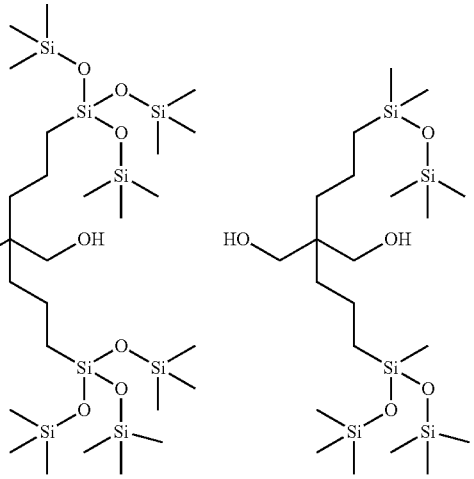

-continued
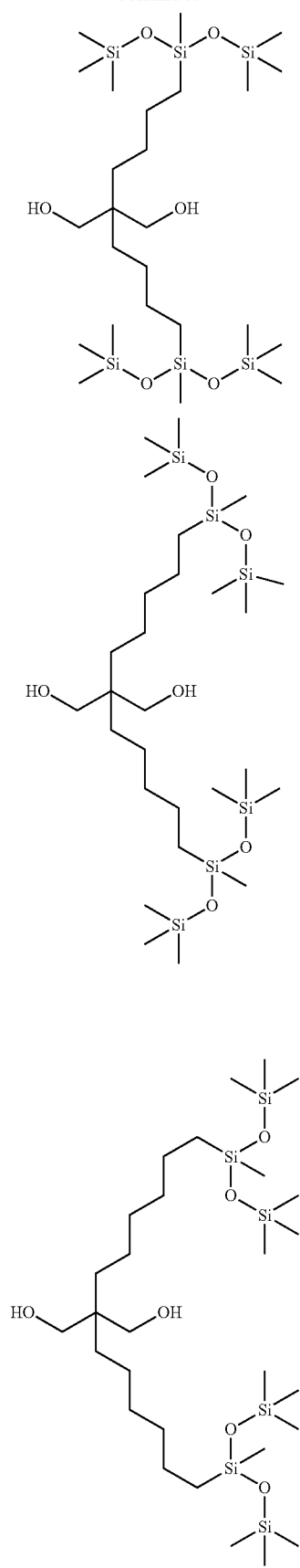
-continued
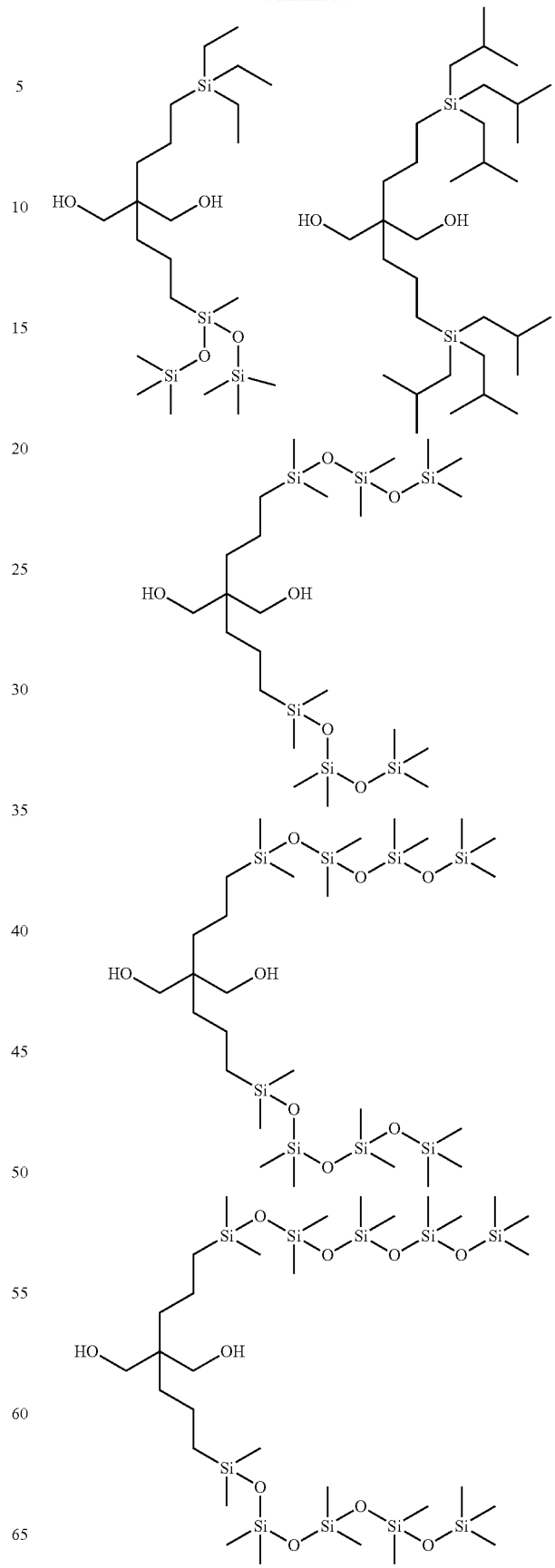

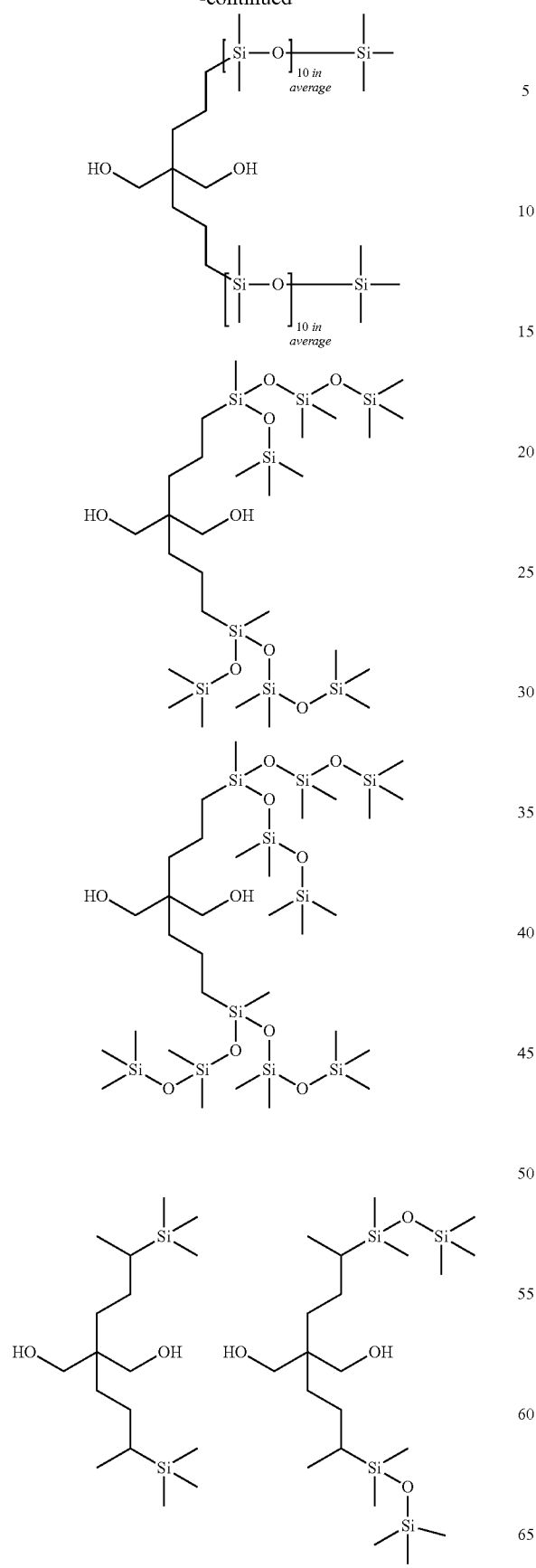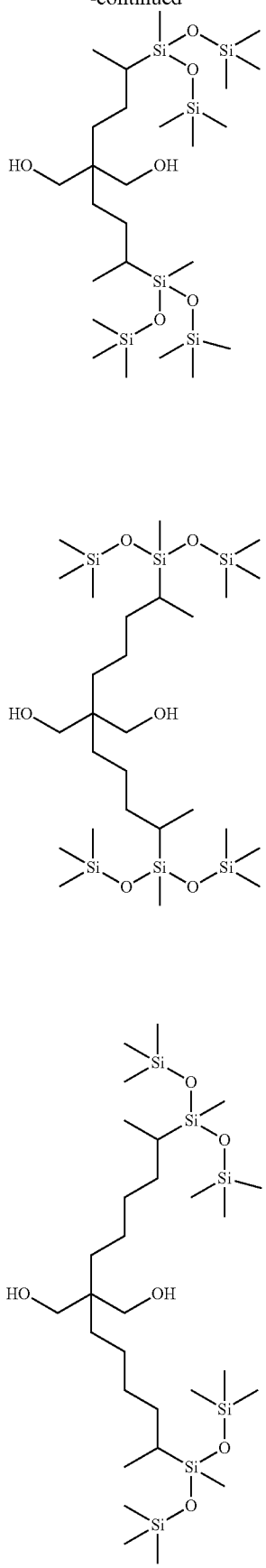

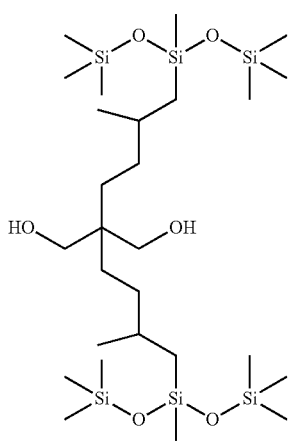
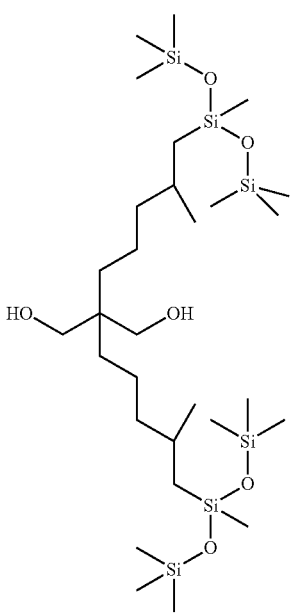
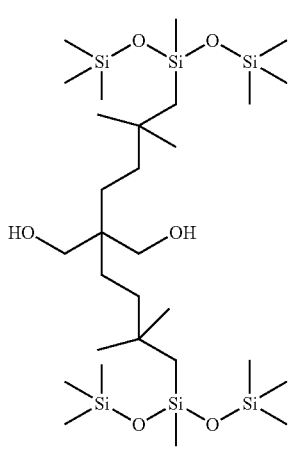
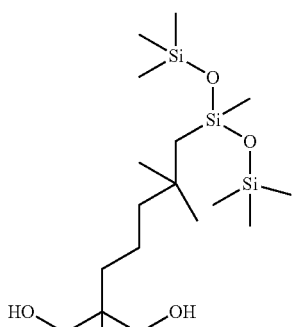
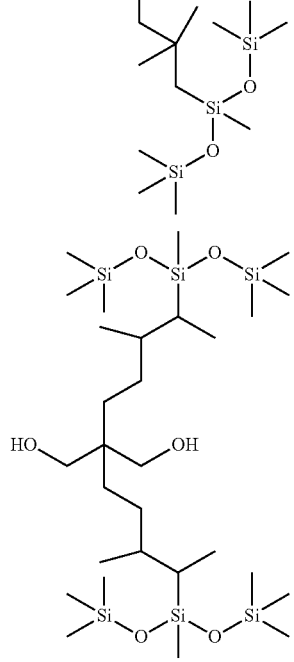
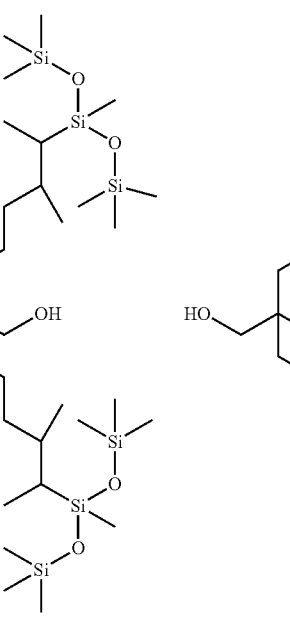

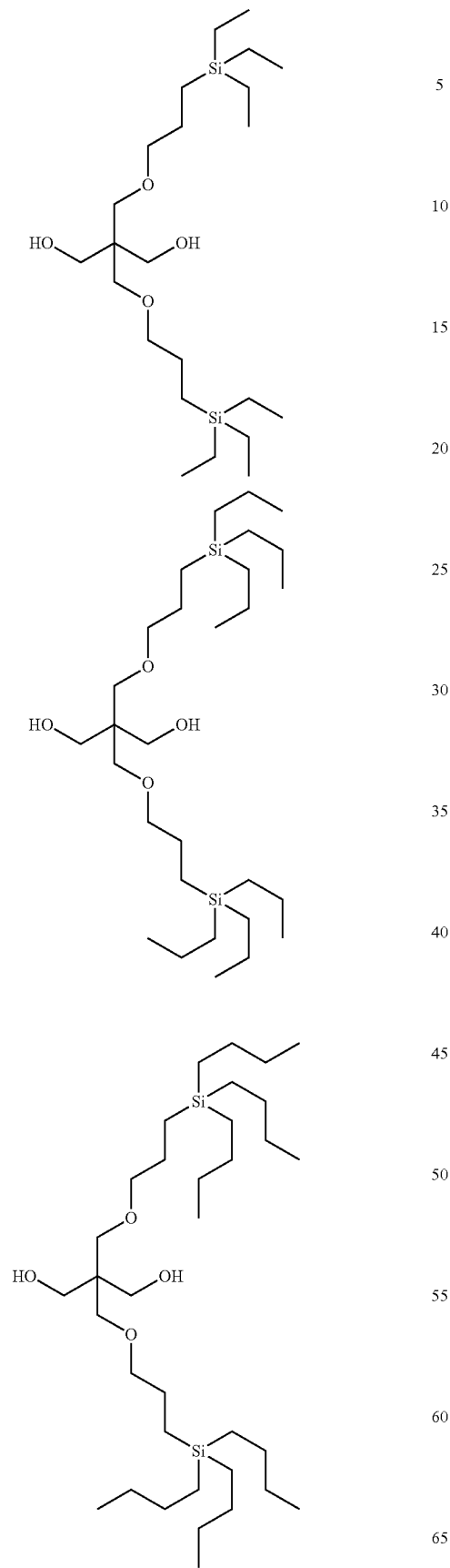

-continued
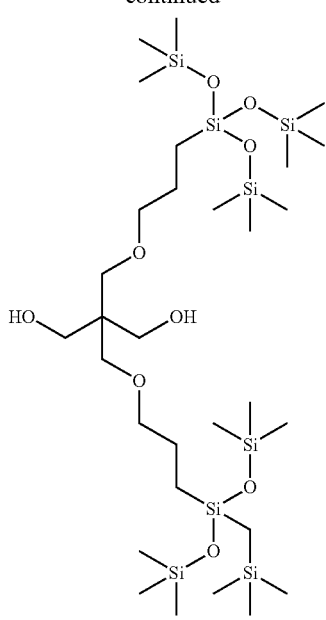
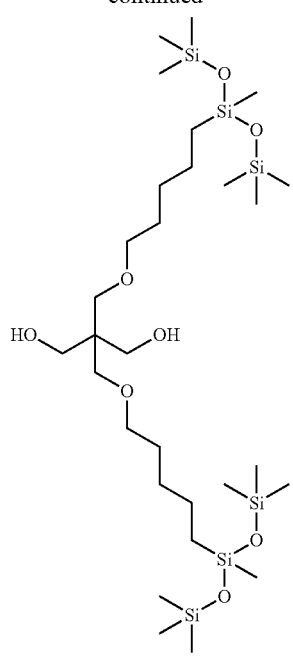
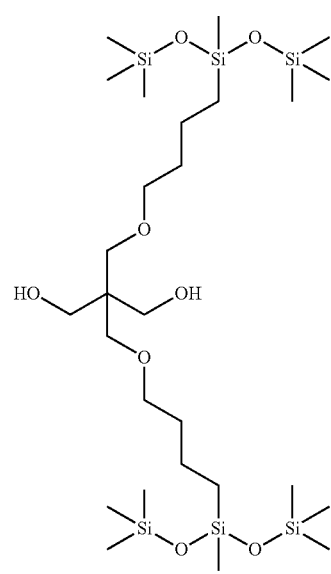
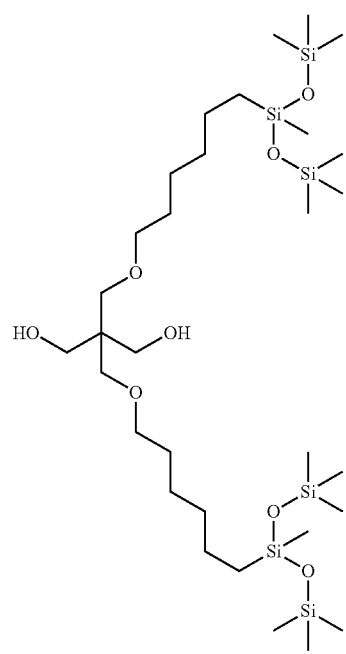

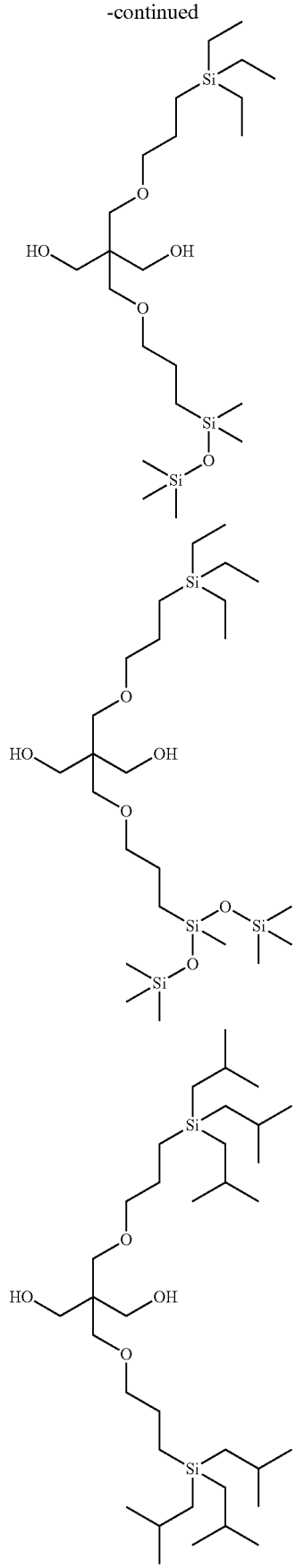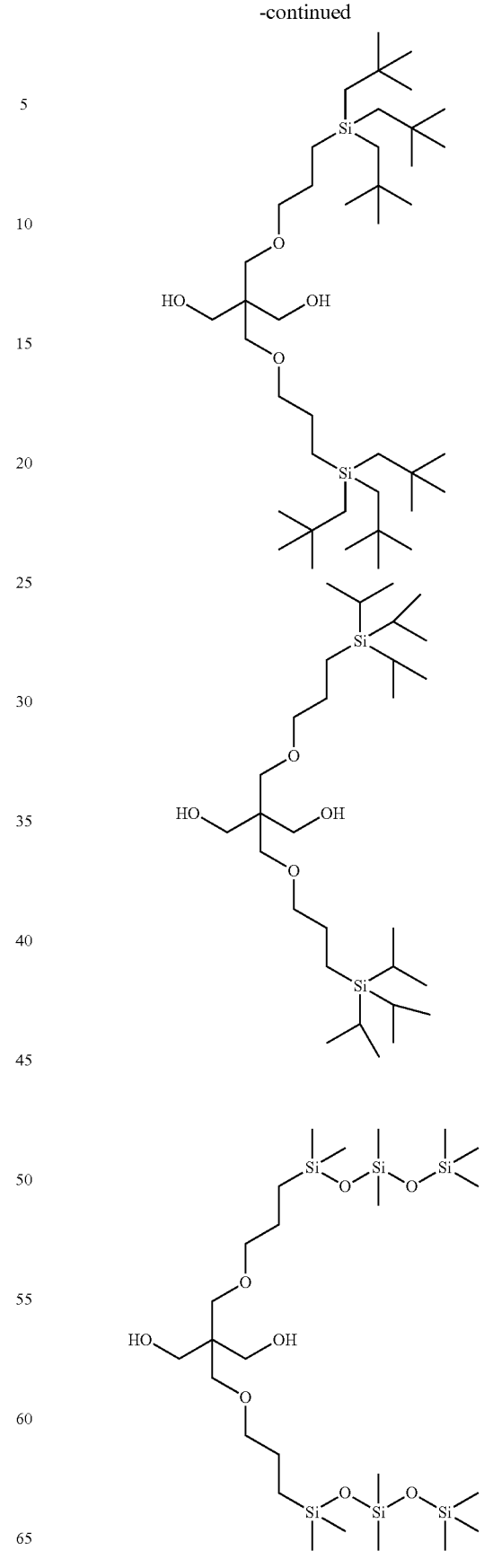

-continued
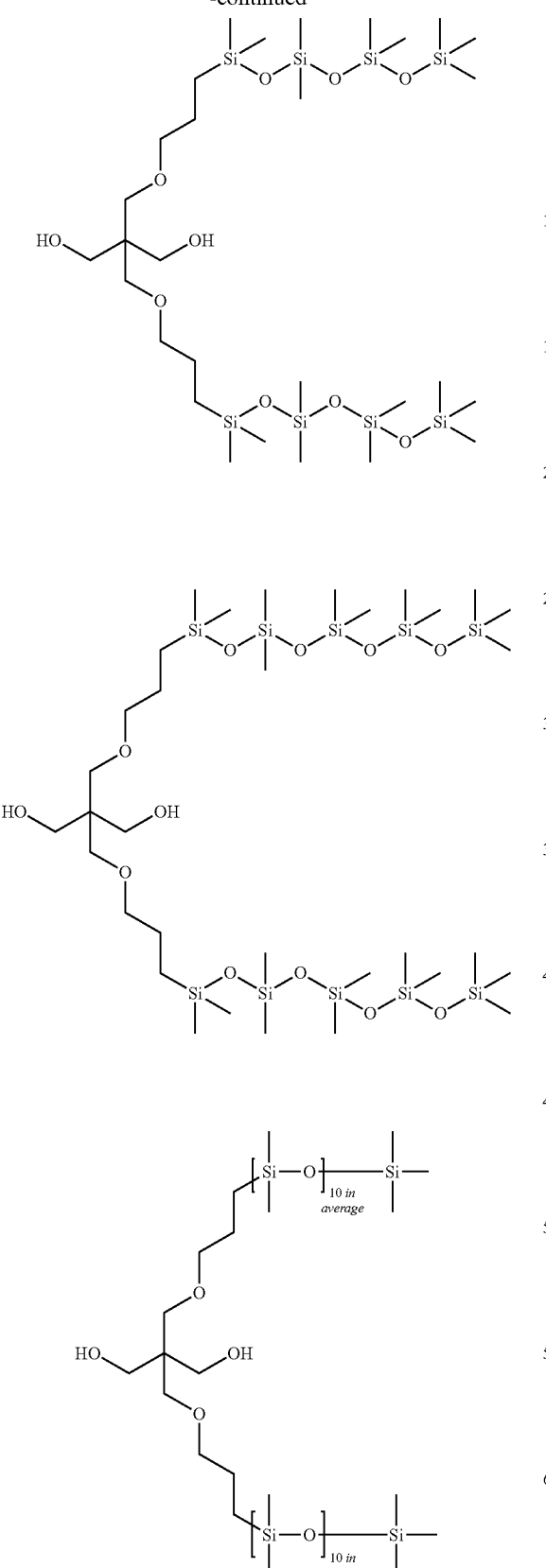

-continued
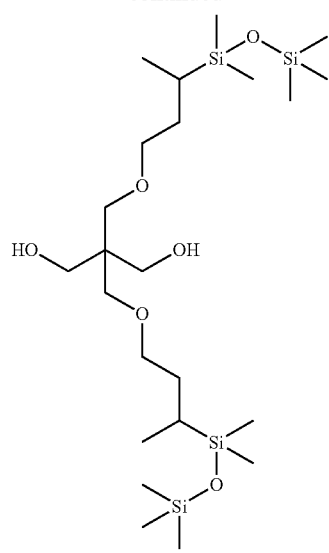
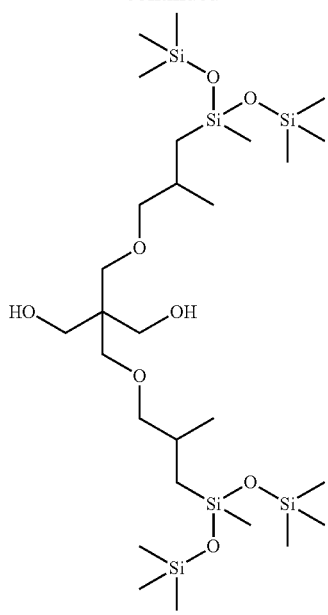 [SMILES: CC(C)(COCC(CO)(CO)COCC(C)(C)C[Si](C)(O[Si](C)(C)C)O[Si](C)(C)C)C[Si](C)(O[Si](C)(C)C)O[Si](C)(C)C]
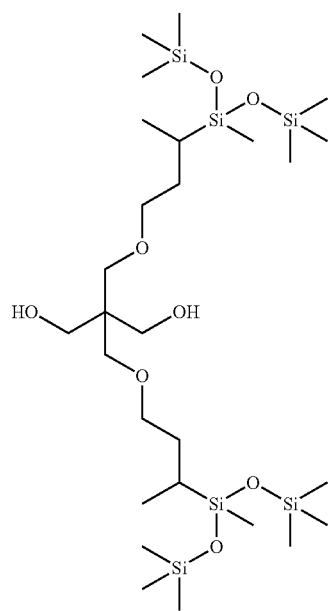
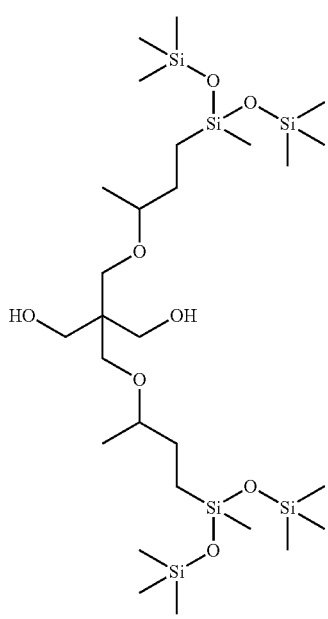

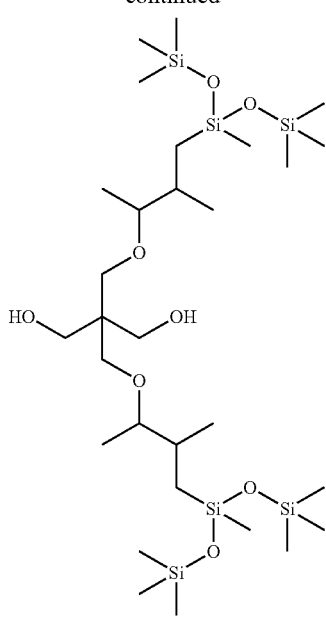
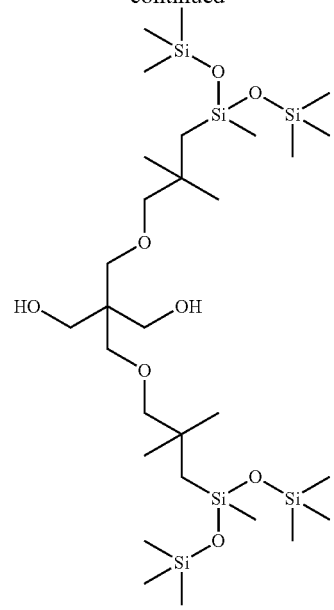
To obtain the polycarbonate soft segment of the repeating unit b1 in the general formula (2), terminal diol polycarbonate compounds illustrated below can be used as the raw material.
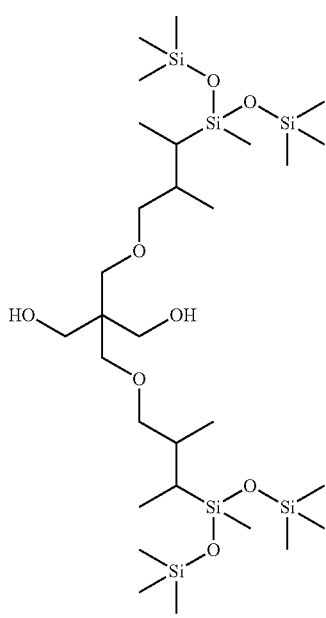
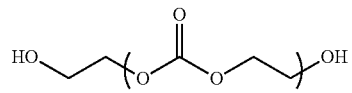
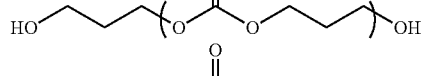
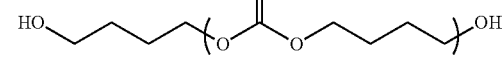
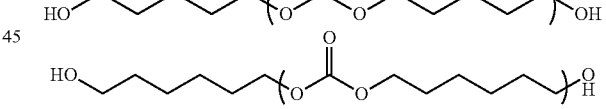
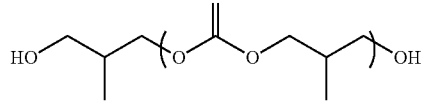
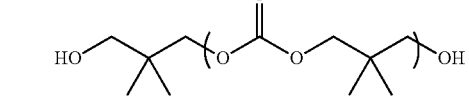
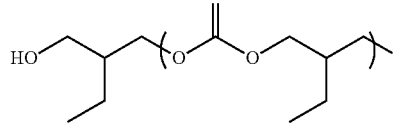
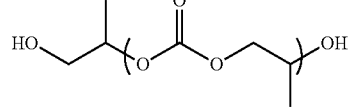

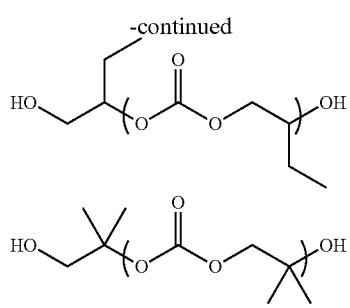
Here, the numbers of the parenthesized repeating units are 1 to 200.
Examples of a terminal diol polyester compound for obtaining the copolymerizable polyester soft segment b2 include the following.
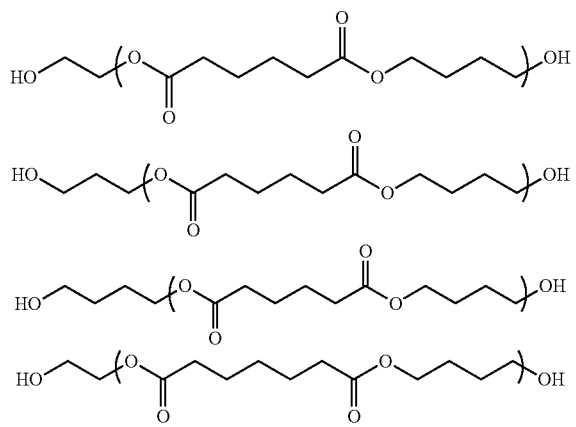
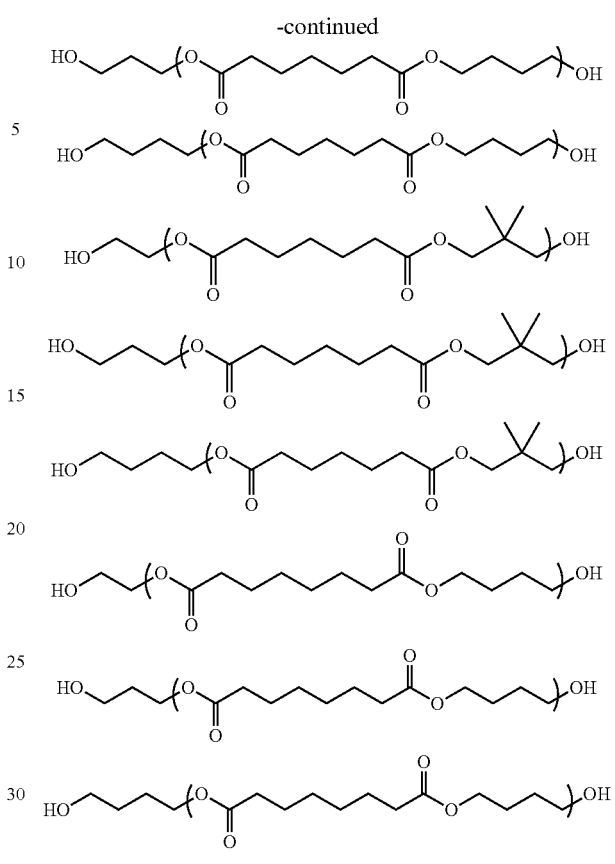
Examples of a terminal diol polyester compound for obtaining the copolymerizable polyester soft segment b3 include the following.
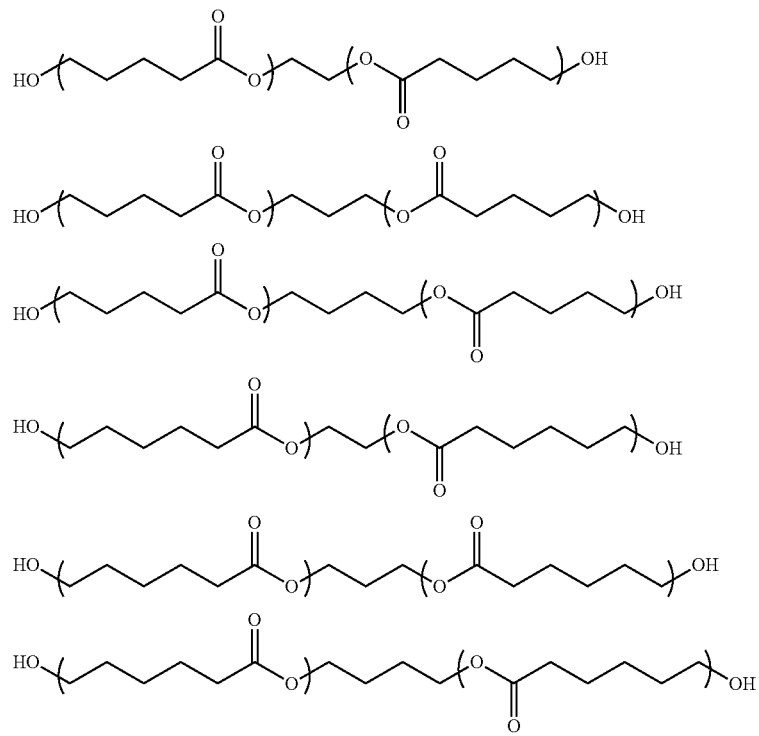

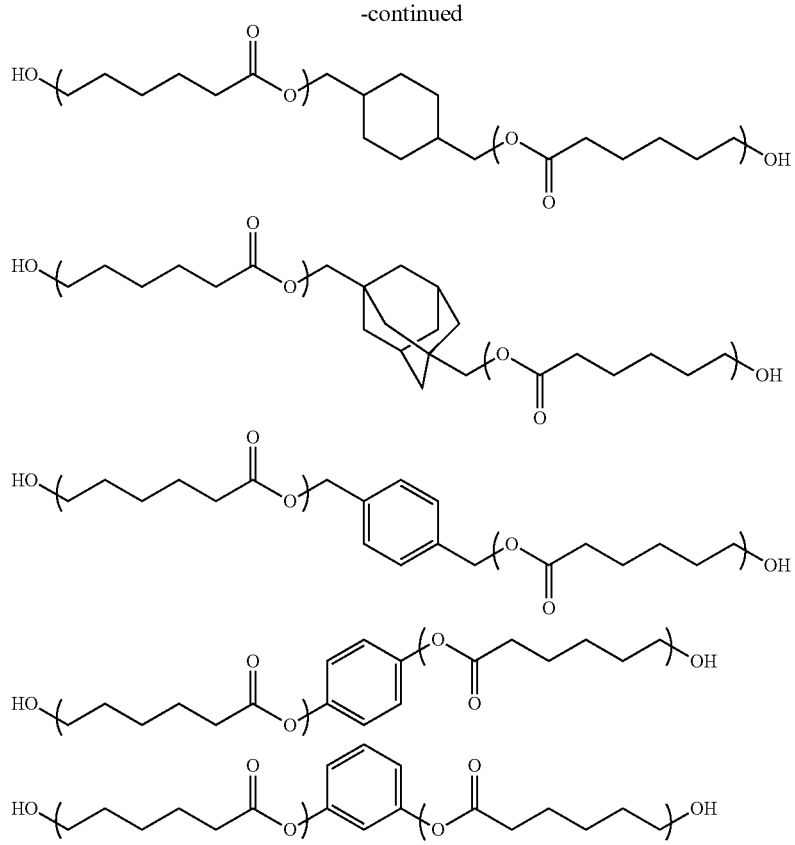

Examples of a terminal diol polyester compound for obtaining the copolymerizable polyester soft segment b4 include the following.

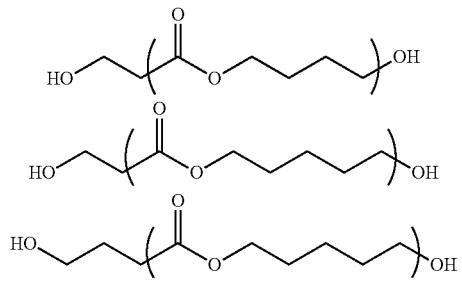

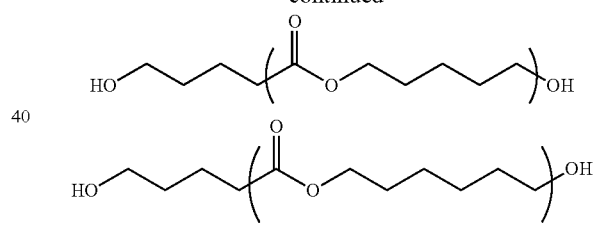

Moreover, the above-described silicone polyurethane resin can also be copolymerized with another polyester soft segment b5 besides b2 to b4. Examples of a terminal diol polyester compound for obtaining the soft segment b5 include the following.

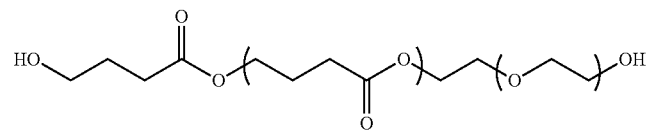

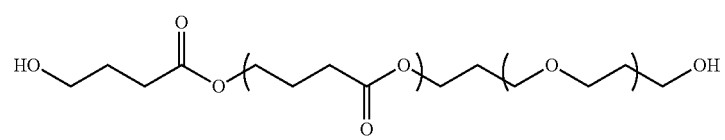

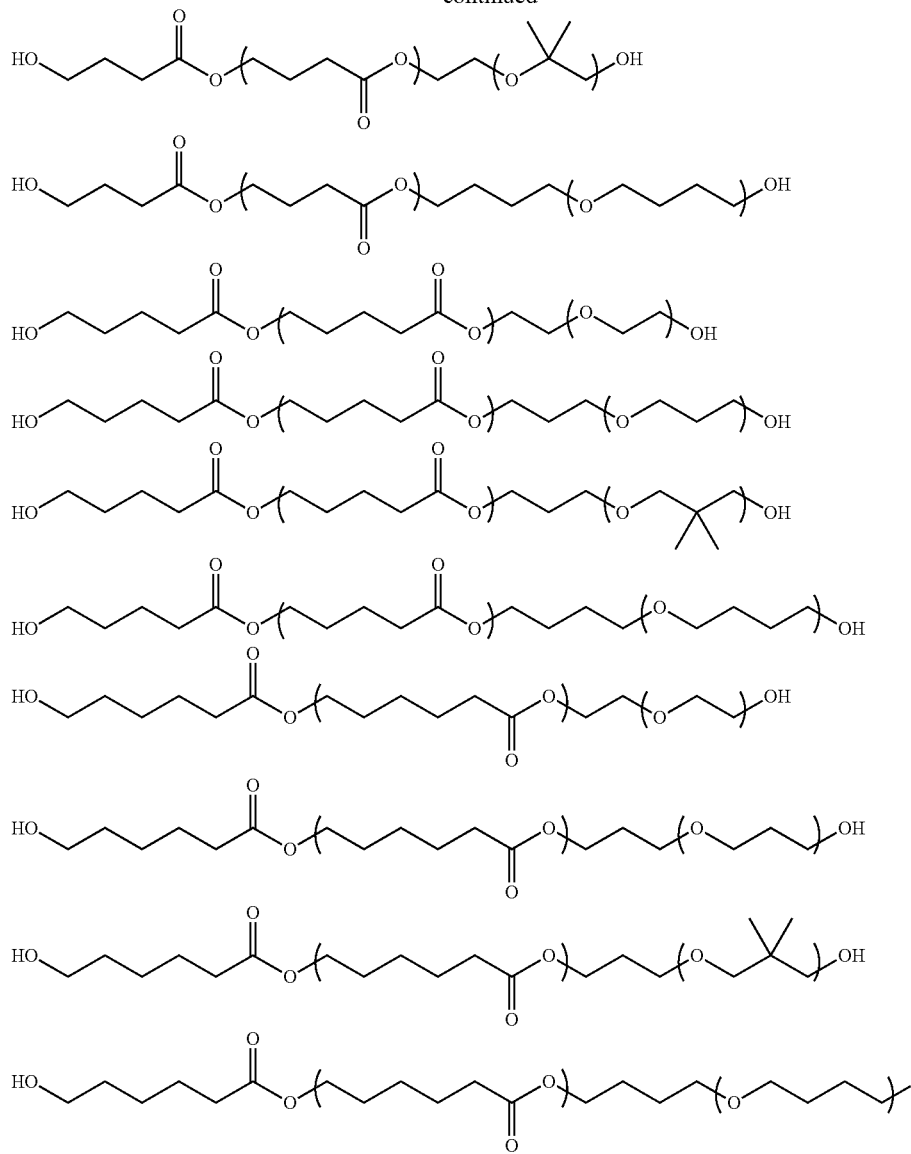
The silicone polyurethane resins each may be copolymerized with a repeating unit d for obtaining the polyether soft segments. To obtain the polyether soft segments, terminal diol polyether compounds illustrated below can also be used for the copolymerization.
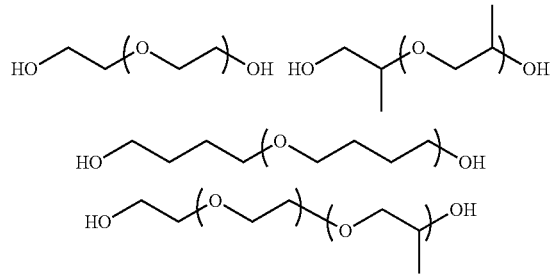
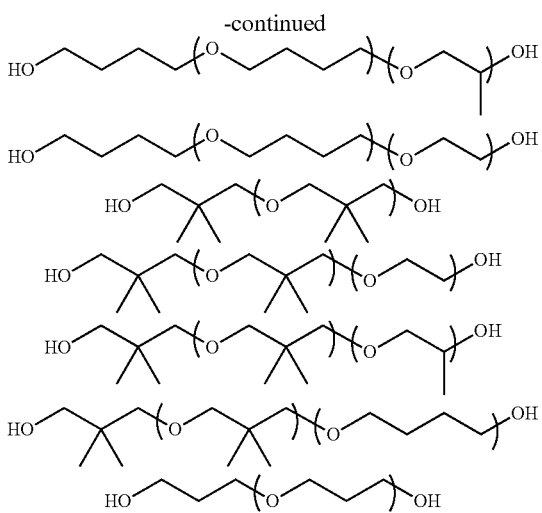

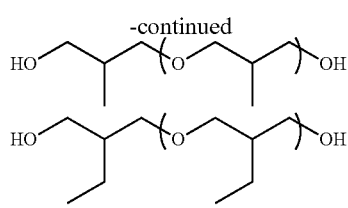

Here, the numbers of the parenthesized repeating units are 1 to 200.

The silicone pendant polyurethane resin having the structure(s) shown by a1 and/or a2 in the general formula (1) used in the stretchable film (A) adopted in the present invention can be formed by reaction between an isocyanate compound and a raw material including the diol compounds having a silicon-containing group(s) shown by the general formulae (a)-1' and (a)-2'. Further, to these, a polycarbonate compound, a polyether compound, and/or a polyester compound which have hydroxy groups at terminals may be added as a chain extender(s) for the reaction with the isocyanate compound to thereby form the silicone pendant polyurethane resin.

Specific examples of the isocyanate compound to be reacted with the diol compounds having a silicon-containing group(s) as well as the polyether compound, the polycarbonate compound, and the polyester compound which have hydroxy groups at terminals include the following.

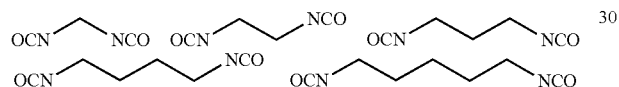
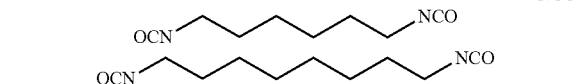
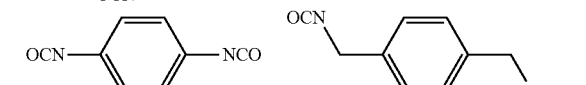
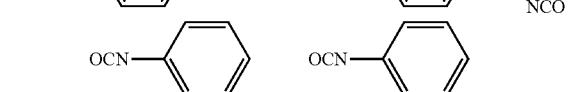
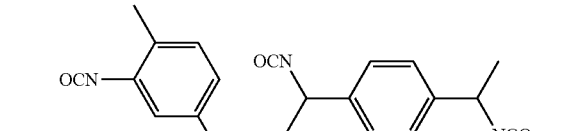
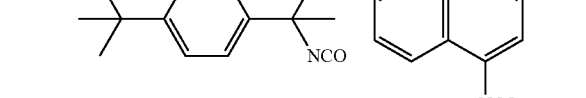

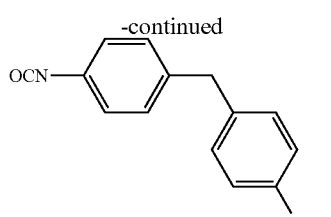
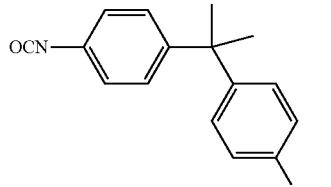
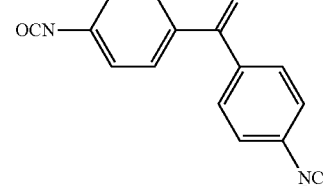
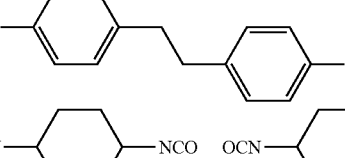
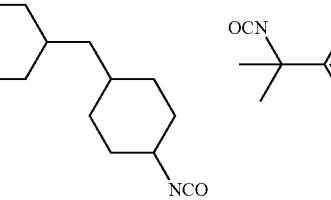
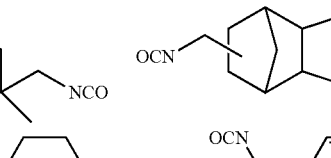
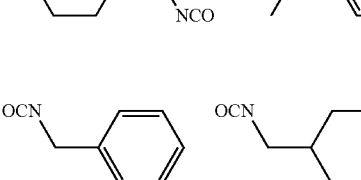
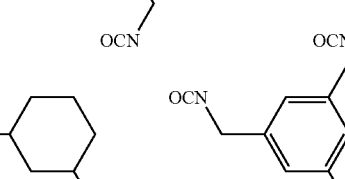

47
-continued
48
-continued
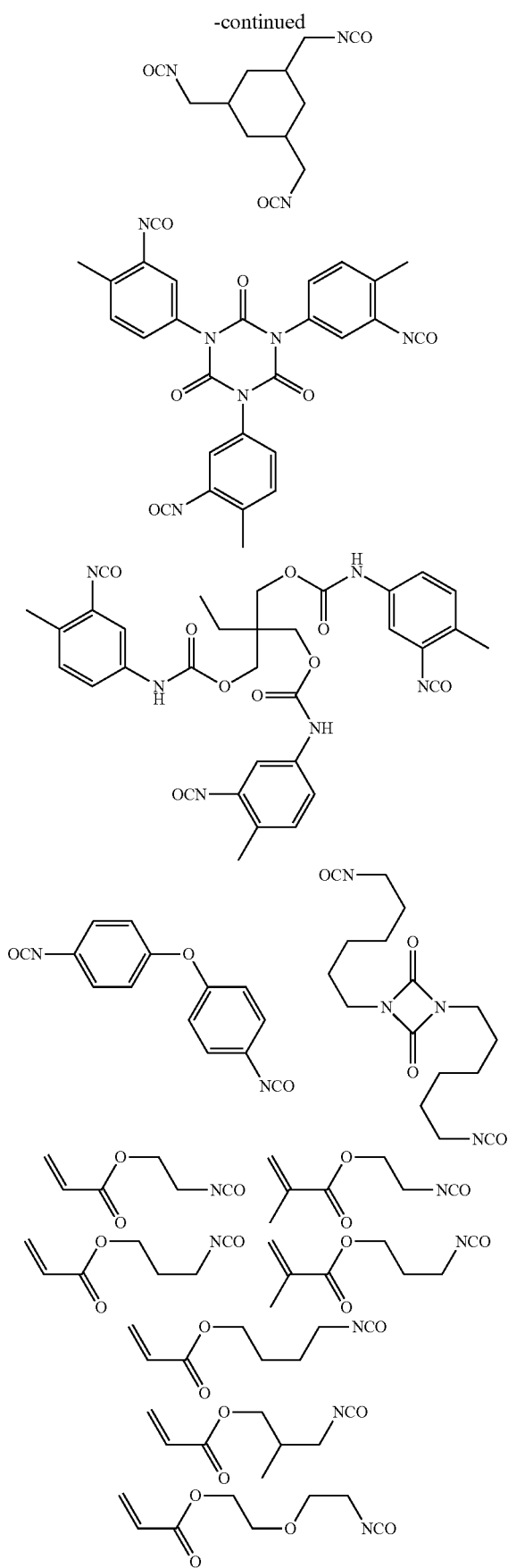
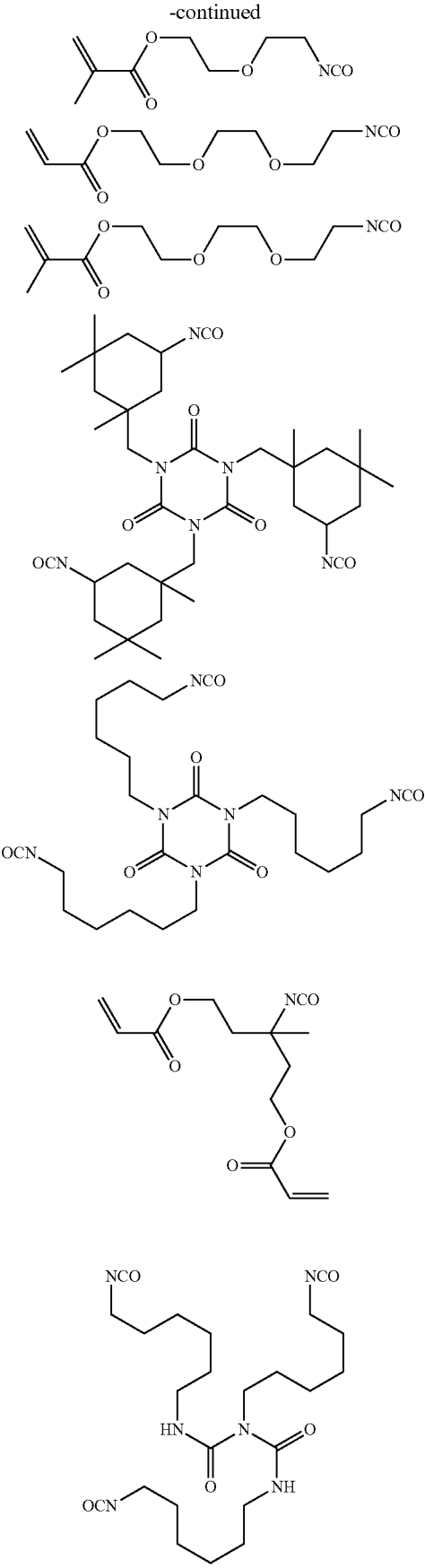

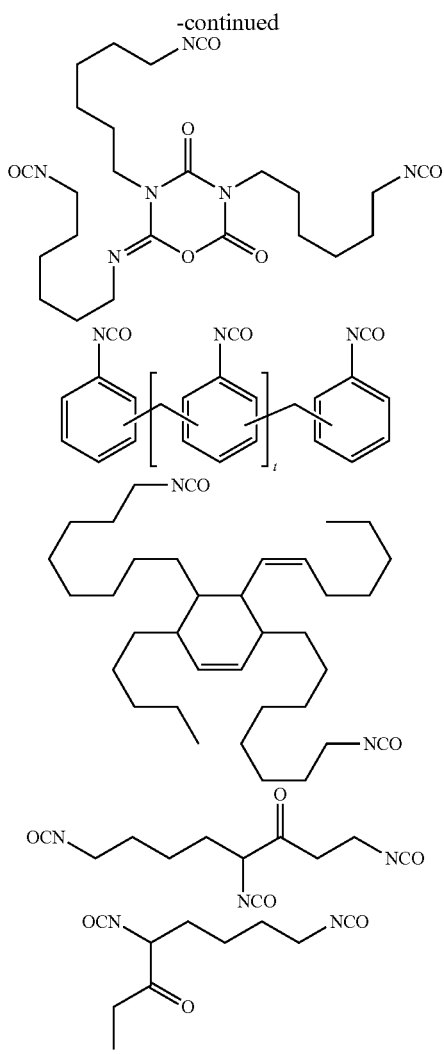

where "t" is an integer of 1 or more.

Among the above isocyanate compounds, particularly an isocyanate compound having a (meth)acrylate group can give the unit c, that is, a compound having a (meth)acrylate group at a terminal shown by the general formula (3), through the reaction with the diol compounds having a silicon-containing group(s) shown by the general formulae (a)-1', (a)-2', and/or the polyether compound, the polycarbonate compound, and the polyester compound which have hydroxy groups at terminals. Besides, the compound having a (meth)acrylate group at a terminal shown by the general formula (3) can also be obtained through a reaction between an isocyanate compound and a compound having a (meth) acrylate group with a hydroxy group.

The aforementioned isocyanate compounds have high reactivity with the diol compounds having a silicon-containing group(s) shown by the general formulae (a)-1', (a)-2' and the polyether compound, the polycarbonate compound, and the polyester compound which have hydroxy groups at terminals; hence, the reaction is sometimes difficult to control. Additionally, the isocyanate compounds react with moisture in the air to inactivate the isocyanate groups during the storage in some cases, and hence have to be carefully stored, for example, with sufficient moisture-proofing. Accordingly, in order to prevent these phenomena, a compound having a blocked isocyanate group may be used in which the isocyanate group is protected with a substituent.

The blocked isocyanate group is a blocked group that is deprotected by heating to be an isocyanate group. Specific examples thereof include isocyanate groups substituted with alcohol, phenol, thioalcohol, imine, ketimine, amine, lactam, pyrazole, oxime, β-diketone, and the like.

A catalyst may be added to decrease the temperature for deprotecting the blocked isocyanate group. Known examples of this catalyst include organic tin such as dibutyltin dilaurate, bismuth salts, and zinc carboxylate such as zinc 2-ethylhexanoate and zinc acetate.

Particularly, Japanese Patent Laid-Open Publication No. 2012-152725 shows that it is possible to decrease the temperature for deprotection reaction by including zinc carboxylate of α,β-unsaturated carboxylic acid as a blocked isocyanate dissociation catalyst.

Further, a compound having an amino group can also be added. When an isocyanate group reacts with an amino group, a urea bond is formed. The moiety of a urethane bond and a urea bond is called as a hard segment, and improves the strength through their hydrogen bonds. Thus, the strength is successfully improved by the addition of urea bonds not only by urethane bonds.

The silicone polyurethane resin used in the stretchable film (A) adopted in the present invention preferably has a weight average molecular weight of 500 or more. Such resins are favorably usable in the stretchable film used in the present invention. The upper limit value of the weight average molecular weight of the silicone polyurethane resin is preferably 500,000 or less.

The top surface film (surface layer) of the stretchable film used in the present invention is preferably a cured product of the stretchable film material containing the silicone side-chain type polyurethane resin having soft segments of the polycarbonate and polyester units b1 to b4 in the general formula (2). Furthermore, the top surface film (surface layer) of the stretchable film may have the other polyester unit b5 and/or polyether unit d besides the units b1 to b4. In this case, the units b1 to b4 account for preferably 10% or more, more preferably 20% or more, of the composition prepared in the urethane polymerization.

Note that the stretchable film preferably has a stretching property of 20 to 1000% in a tensile test stipulated according to JIS K 6251. Such a stretching property enables particularly favorable use as a substrate film for a stretchable wiring.

<Stretchable Wiring Film>

The inventive stretchable wiring film is a stretchable wiring film including: (A) a stretchable film made of, at least as a top surface thereof, a cured product of a stretchable film material containing a silicone polyurethane resin, in which the top surface of the stretchable film has a repeated uneven pattern formed with depths of 0.1 μm to 5 mm and pitches of 0.1 μm to 10 mm; and (B) a stretchable wiring which is formed on the top surface of the stretchable film where the repeated uneven pattern is formed.

FIG. 2 shows an example of the inventive stretchable wiring film. As shown in FIG. 2(a), a stretchable wiring film 14 of the present invention may include a stretchable wiring 13 that is formed on the top surface of the stretchable film 6 shown in FIG. 1(a) where a repeated uneven pattern is formed. Additionally, as shown in FIG. 2(b), the inventive stretchable wiring film 14 may include the stretchable wiring 13 formed on the top surface of the stretchable film 6 where a repeated uneven pattern is formed. The stretchable film 6 has the portion 12 other than the top surface shown in FIG.

1(b). Furthermore, as will be described later, multiple layers of stretchable wirings may be formed with an insulator film provided between the stretchable wirings.

Moreover, the stretchable wiring film preferably has an elongation percentage in a range of 5 to 500%. Such a stretchable wiring film is favorably usable for a bio-electrode, for example.

The stretchable wiring film preferably has a stretchable film configured to cover a stretchable wiring. In this case, the stretchable film configured to cover a stretchable wiring is more preferably a cured product of a stretchable film material containing the silicone-pendant type polyurethane resin having a structure shown by the general formula (1). In such a stretchable wiring film, the stretchable wiring is covered with the stretchable film having higher strength.

The stretchable film having the uneven top surface used in the inventive stretchable wiring film as described above can make the stretchable wiring film have excellent hysteresis, stretchability and strength that are equivalent to those of polyurethane, together with a film top surface having excellent water repellency equivalent to that of silicone and being free from stickiness. Further, such a stretchable wiring film has less decrease in electric conductivity when stretched.

<Method for Forming Stretchable Wiring Film>

The present invention also provides a method for forming a stretchable wiring film, including the steps of:

(1) applying a stretchable film material containing a silicone-pendant type polyurethane resin having a structure shown by the following general formula (1) onto a substrate having a repeated uneven pattern formed with depths of 0.1 μm to 5 mm and pitches of 0.1 μm to 10 mm;

(2) curing the stretchable film material by heating and/or light irradiation;

(3) peeling a cured product of the stretchable film material from the substrate to form a stretchable film having a top surface with the repeated uneven pattern; and (4) applying a stretchable electro-conductive paste onto the top surface of the stretchable film where the repeated uneven pattern is formed to form a stretchable wiring,

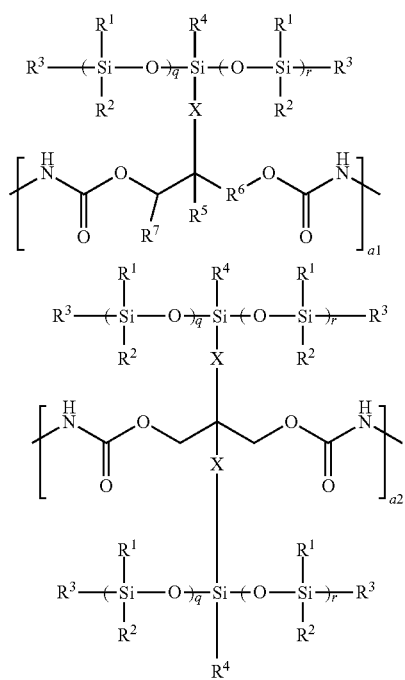

(1)

where $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a —(OSiR$^1$R$^2$)$_s$—OSiR$^1$R$^2$R$^2$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2≤1.0.

In this event, the inventive method may include, between the step (1) and the step (2), (1') a step of pressure-bonding a polyurethane film onto the stretchable film material.

Alternatively, the inventive method may include, between the step (2) and the step (3), (2'-1) a step of coating the cured product of the stretchable film material with a stretchable film material containing a polyurethane resin, and (2'-2) a step of curing the stretchable film material containing the polyurethane resin by heating and/or light irradiation to form a polyurethane film.

In this respect, FIG. 4 shows an example of the process of forming the inventive stretchable wiring film. A substrate 7' is prepared to have a cross section as shown in FIG. 4(a) in which a repeated pattern is formed. Onto the substrate 7' having the repeated pattern, a stretchable film material 8 containing a silicone-pendant type polyurethane resin having a structure shown by the general formula (1) is applied as shown in FIG. 4(b) and cured by heating and/or light irradiation. A cured product of the stretchable film material 8 is peeled from the substrate 7'. Thus, as shown in FIG. 4(c), a stretchable film 6 having the repeated uneven pattern formed on the top surface can be obtained. Then, a stretchable electro-conductive paste is applied onto the top surface to form a wiring pattern (stretchable wiring 13) as shown in FIG. 4(d), thereby forming a stretchable wiring film 14.

Next, FIG. 5 shows another example of the inventive method for forming a stretchable wiring film. A substrate 7' having a repeated pattern as shown in FIG. 5(a) is prepared. Next, as shown in FIG. 5(b), a stretchable film material 8 containing a silicone pendant polyurethane resin shown by the general formula (1) is applied onto the substrate 7', and a polyurethane film 9 is disposed on the stretchable film material 8. The stretchable film material 8 is cured by heating and/or light irradiation, so that a cured product 11 can be obtained. Then, as shown in FIG. 5(c), this cured product 11 is peeled, so that a stretchable film 6 having the repeated uneven pattern formed on the top surface can be obtained. Then, a stretchable electro-conductive paste is applied onto the top surface to form a wiring pattern (stretchable wiring 13) as shown in FIG. 5(d), thereby forming a stretchable wiring film 14.

The polyurethane film 9 to be disposed on the top does not necessarily have to contain silicon, but preferably contains silicon from the viewpoint of high water repellency. The polyurethane film to be disposed on the top may be a commercially-available thermoplastic polyurethane (TPU) film. Moreover, since the polyurethane to be disposed on the top requires high stretchability, the polyurethane preferably contains a polyether or polyester soft segment.

Next, FIG. 6 shows still another example of the inventive method for forming a stretchable wiring film. On a stretchable substrate (polyurethane film 9) shown in FIG. 6(a), a uneven pattern made of a stretchable film material 8 is directly formed by ejection through inkjet printing or the like as shown in FIG. 6(b) and then cured by light irradiation, so that the uneven pattern made of a cured product 11 of the stretchable film material is formed as shown in FIG. 6(c). This method does not necessarily require a printing plate and thus can improve the throughput. Since the ejected ink flows to flatten the unevenness, it is necessary to cure the ink immediately after the ejection. The curing is performed preferably by light irradiation which is capable of instant curing, or preferably with an LED laser capable of pinpoint curing in synchronism with the movement of the ink jet nozzle. Then, a stretchable electro-conductive paste is applied onto the uneven pattern to form a wiring pattern (stretchable wiring 13) as shown in FIG. 6(d), thereby forming a stretchable wiring film 14.

Next, FIG. 7 shows still another example of the inventive method for forming a stretchable wiring film. A substrate 7' having a repeated pattern as shown in FIG. 7(a) is prepared. Next, after a stretchable film material 8 containing a silicone pendant polyurethane resin shown by the general formula (1) is applied and cured, a polyurethane material 10 (a stretchable film material containing a polyurethane resin) may be applied and cured as shown in FIG. 7(b). Then, as shown in FIG. 7(c), the polyurethane material 10 is peeled, so that a stretchable film 6 having the repeated uneven pattern formed on the top surface can be obtained. Then, a stretchable electro-conductive paste is applied onto the top surface to form a wiring pattern (stretchable wiring 13) as shown in FIG. 7(d), thereby forming a stretchable wiring film 14.

The polyurethane material 10 to be applied on the top does not necessarily have to contain silicon, but preferably contains silicon from the viewpoint of high water repellency. Moreover, since the polyurethane to be applied on the top requires high stretchability, the polyurethane resin preferably contains a polyether or polyester soft segment.

Next, FIG. 8 shows an example of the inventive method for forming a stretchable wiring film in which multiple wires are formed and an insulator film is disposed between the wires. To prepare a stretchable wiring film having multiple wires with an insulator film disposed between the wires, first, a stretchable film material 8 is applied onto a uneven substrate 7' as shown in FIG. 8(e). Then, as shown in FIG. 8(f), the stretchable wiring film 14 prepared in FIG. 4(d) is mounted on the stretchable film material 8 and cured. As shown in FIG. 8(g), the film is peeled from the substrate 7'. Then, a stretchable wiring 13 is prepared on the film. Thus, two wires with the insulator film inserted therebetween are prepared as shown in FIG. 8(h). Further, the second wire may be coated with a silicone pendant polyurethane as shown in FIG. 8(i). Additionally, the stretchable wiring 13 prepared in FIG. 4(d) may be coated with a silicone pendant polyurethane.

As a method for forming a stretchable film in the present invention, on a printing plate with a repeated uneven pattern, a stretchable film material containing a silicone pendant polyurethane resin shown by the general formula (1) may be applied, cured, and peeled to form a stretchable film. The printing plate with a repeated uneven pattern (a substrate having a repetitive pattern formed thereon) to be used is preferably made of glass, quartz, metal, Teflon(registered trademark), polyethylene, or polypropylene.

Particularly, when the substrate having a repeated pattern formed thereon is made of quartz, the stretchable film material can be cured by light irradiation through the quartz surface. This curing method is the same as flash nano-imprinting lithography. To improve the release characteristics, the printing plate may be coated with a release agent, or a printing plate surface-treated with an alkoxysilane compound having a fluoroalkyl group may be used. As the release agent, a fluorine-based surfactant or a silicone-based surfactant is preferably used.

The pattern depth ranges from 0.1 µm to 5 mm, and the pattern pitch ranges from 0.1 µm to 10 mm. The pattern may have a wavy cross section as shown in FIG. 4(a), or the cross section may have triangular, trapezoidal, concave lens-like, convex lens-like, or quadrangular shapes. A wavy shape (a corrugated shape) is preferable from the viewpoints of filling and release characteristics of the silicone pendant polyurethane.

When the uneven pattern is observed from the above, the layout may be, for example: a row of lines such as vertical, horizontal, oblique, wavy, or radial lines, or combinations thereof; combinations of these lines that intersect with each other in a lattice form or similar other forms; and holes or protrusions arranged in a circular, elliptical, triangular, quadrangular, pentagonal, or hexagonal shape.

Examples of the method for applying the stretchable film material onto the substrate having the repeated pattern include spin coating, bar coating, roll coating, flow coating, dip coating, spray coating, doctor coating, screen printing, inkjet printing, and the like.

The uneven pattern can be formed on a stretchable substrate with a 3D printer by inkjet printing or nozzle ejection. Light irradiation immediately after the ejection from the nozzle onto the stretchable substrate enables the formation of the uneven pattern without deformation. In this case, since a printing plate is not required, the productivity is high. For the light irradiation, it is possible to use not only a UV lamp but also an LED. Pinpoint UV irradiation with an LED laser is preferable because desired shapes can be formed at will in combination with inkjet printing.

Note that the viscosity of the stretchable film material (mixture solution) can be controlled as appropriate. To decrease the viscosity, for example, an organic solvent is mixed; to increase the viscosity, for example, a filler such as silica is mixed.

The organic solvent is preferably an organic solvent having a boiling point in a range of 100 to 300° C. at atmospheric pressure. Specifically, it is preferable to use one or more selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, dimethyl oxalate, diethyl oxalate, dipropyl oxalate, dibutyl oxalate, dimethyl malonate, diethyl malonate, dipropyl malonate, dibutyl malonate, dimethyl maleate, diethyl maleate, dipropyl maleate, dibutyl maleate, dimethyl succinate, diethyl succinate, dipropyl succinate, dibutyl succinate, dimethyl glutarate, diethyl glutarate, dipropyl glutarate, dibutyl glutarate, dimethyl adipate, diethyl adipate, dipropyl adipate, dibutyl adipate, toluene, dimethylbenzene, cumene, n-butylbenzene, tert-butylbenzene, and anisole.

These organic solvents can be used in the stretchable electro-conductive paste, too.

Embodiment 1

As a method for forming a layer having a repeated uneven pattern as described above, for example, a network of a polycarbonate- or polyester-containing silicone pendant polyurethane is formed on a printing plate with a repeated uneven pattern, concurrently cured by heating or light irradiation, and peeled from the printing plate.

In this event, it is preferable to form a uneven stretchable film by: mixing the polycarbonate compound or the polyester compounds for forming the units b1 to b4 in the general formula (2), the silicone pendant diol compound for forming the unit a1 or the unit a2, a compound having an isocyanate group, optionally a polyether diol compound or a polyester diol compound for chain extension, an amine compound, a compound having three or more hydroxy groups as a cross-linking agent, and a catalyst; forming a film of this stretchable film material mixture on the printing plate with a repeated uneven pattern; and curing the film by heating.

In this method, a polymer network is formed by forming urethane bonds through the reaction of the isocyanate groups and the hydroxy groups, and increasing the molecular weight simultaneously. When compounds having three or more hydroxy groups or isocyanate groups are added, cross-link reaction proceeds, thereby lowering the stretchability but improving the film strength. Accordingly, it is possible to control the hardness, stretchability, and strength by controlling the loading amount of the compounds having two or three hydroxy groups or isocyanate groups. Additionally, an independent stretchable film can be obtained by peeling the film from the substrate after the curing.

Regarding the molar ratio of the hydroxy groups and the isocyanate groups in the stretchable film material (mixture), it is preferable that the hydroxy groups and the isocyanate groups be in the same molar number, or that the molar number of the hydroxy group be larger, that is, the value obtained by dividing the molar number of the hydroxy groups by the molar number of the isocyanate groups be 1 or more. When the molar number of the isocyanate groups is smaller, carbon dioxide cannot be formed through the reaction of excess isocyanate groups with water, thereby preventing voids due to foaming in the film. When foamed urethane is prepared, excess isocyanate groups are present therein. Since the inventive stretchable film requires the property of higher strength, the film is preferably free from void due to foaming.

When a cured product of the stretchable film material is formed in such a state that the molar number of the hydroxy groups is larger than that of the isocyanate groups as described above, the terminal of the polymer sometimes has a urethane bond that is formed only at one side of each diol compound shown by general formulae (a')-1, (a')-2:

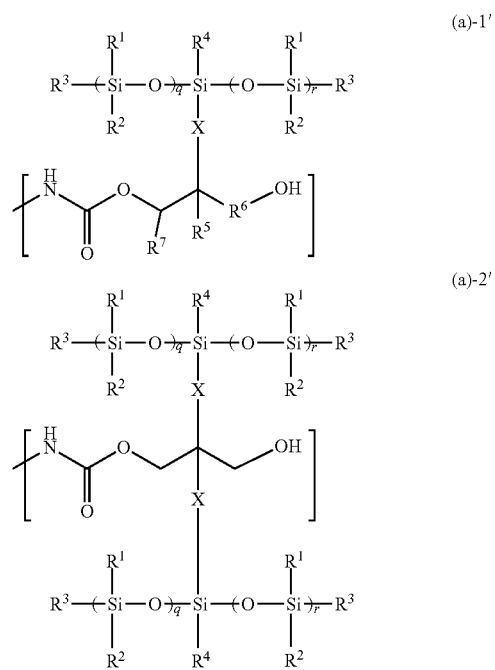

where $R^1$ to $R^7$, X, "q", and "r" are as defined above.

Other than the above-described method, the film can also be formed by a prepolymer method in which a hydroxy group-containing compound and an isocyanate compound are mixed to form a polymer material (prepolymer); then, a hydroxy group-containing compound or an isocyanate group-containing compound is additionally mixed and cured by heating. When the prepolymer is formed, one of the hydroxy group-containing compound and the isocyanate compound is used in an excess amount to increase the molecular weight. This can decrease the amount of unreacted residual isocyanate to decrease the uncrosslinked portion to thus form a film with higher strength compared to the case of one shot method, in which the hydroxy group-containing compound and the isocyanate compound are mixed to form a film at once.

The heating temperature in curing is preferably in a range of room temperature to 200° C., more preferably in a range of 40 to 160° C., for a period of 5 seconds to 60 minutes.

Embodiment 2

Alternatively, the stretchable film having a uneven top surface can also be formed by: synthesizing a urethane polymer through reaction of isocyanate and hydroxy groups; forming a (meth)acrylate group at a terminal of the urethane polymer as shown in the general formula (3); forming a film of this polymer; and curing the film by heating and/or light irradiation.

Specifically, in the case of polycarbonate- or polyester-containing silicone pendant polyurethane acrylate, the polycarbonate or polyester diol compound for obtaining the units b1 to b4 in the general formula (2) and the silicone pendant diol compound for obtaining the unit a1 or a2 are mixed with a protected or unprotected isocyanate compound, and an isocyanate group-containing (meth)acrylate compound or hydroxy group-containing (meth)acrylate. After the polymerization, a polycarbonate- or polyester-containing silicone pendant urethane (meth)acrylate polymer is synthesized which has (meth)acrylate at the polymer terminal.

The polycarbonate- or polyester-containing silicone pendant urethane (meth)acrylate polymer is crosslinked by radical. As a method for radical crosslinking, a radical generator is desirably added. Examples of the radical generator include a thermal-radical generator which generates a radical by thermal decomposition, and a photo-radical generator which generates a radical by light irradiation.

Examples of the thermal-radical generator include azo radical generators and peroxide radical generators. Examples of the azo radical generators include 2,2'-azobisisobutyronitrile (AIBN), 2,2'-azobis(2,4-dimethylvaleronitrile), dimethyl 2,2'-azobis(2-methylpropionate), 2,2'-azobis(4-methoxy-2,4-dimethylvaleronitrile), 2,2'-azobis(cyclohexane-1-carbonitrile), 4,4'-azobis(4-cyanovaleric acid), and the like. Examples of the peroxide radical generators include benzoyl peroxide, decanoyl peroxide, lauroyl peroxide, succinyl peroxide, t-butylperoxy-2-ethylhexanoate, t-butylperoxypivaloate, 1,1,3,3-tetramethylbutylperoxy-2-ethylhexanoate, and the like.

Examples of the photo radical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, 2-phenyl-2-(p-toluenesulfonyloxy)acetophenone (BAPO), and camphorquinone.

Note that the loading amount of the thermal or photo-radical generator is preferably in a range of 0.1 to 50 parts by mass based on 100 parts by mass of the resin in the stretchable film material.

It is also possible to add a crosslinking agent that has a plurality of (meth)acrylate or thiol. This makes it possible to improve the efficiency of radical crosslinking.

The stretchable film material may be mixed with a monomer that has an alkyl group or an aryl group, or a monomer that has an alkyl group or an aryl group substituted with a silicon-containing group or fluorine. These make it possible to form a thinner stretchable film by decreasing the viscosity of the solution. When each monomer has a polymerizable double bond, the monomer can be fixed into the film in curing the film.

Examples of the monomer that has an alkyl group or an aryl group include isobornyl acrylate, lauryl acrylate, tetradecyl acrylate, stearyl acrylate, isostearyl acrylate, behenyl acrylate, adamantane acrylate, phenoxyethylene glycol acrylate, phenoxydiethylene glycol acrylate, and 2 to 6 functional acrylates. Examples of the bifunctional acrylate include 1,6-hexanediol diacrylate, 1,9-nonanediol diacrylate, isononanediol diacrylate, 1,10-decanediol diacrylate, neopentyl glycol diacrylate, 2-hydroxy-3-methacrylpropyl acrylate, diethylene glycol diacrylate, triethylene glycol diacrylate, polyethylene glycol diacrylate, dipropylene glycol diacrylate, tripropylene glycol diacrylate, polypropylene glycol diacrylate, polytetramethylene glycol diacrylate, polyethylene polypropylene glycol diacrylate, dioxane glycol diacrylate, tricyclodecanedimethanol diacrylate, 9,9-bis[4-(2-hydroxyethoxy)phenyl]fluorene diacrylate, ethoxylated bisphenol A diacrylate, propoxylated bisphenol A diacrylate, and ethoxylated propoxylated bisphenol A diacrylate. Examples of the trifunctional acrylate include trimethylolpropane triacrylate, ethoxylated trimethylolpropane triacrylate, propoxylated trimethylolpropane triacrylate, glycerin triacrylate, ethoxylated glycerin triacrylate, propoxylated glycerin triacrylate, tris(2-acryloxyethyl)isocyanurate, caprolactone modified tris(2-acryloxyethyl)isocyanurate, and pentaerythritol triacrylate. Examples of the tetrafunctional acrylate include pentaerythritol tetraacrylate, ethoxylated pentaerythritol tetraacrylate, propoxylated pentaerythritol tetraacrylate, ditrimethylolpropane tetraacrylate, ethoxylated ditrimethylolpropane tetraacrylate, and propoxylated ditrimethylolpropane tetraacrylate. Examples of the penta- or hexa-functional acrylate include dipentaerythritol polyacrylate, ethoxylated dipentaerythritol polyacrylate, and propoxylated dipentaerythritol polyacrylate. It is also possible to use these monomers in which each acrylate is replaced by methacrylate.

When the stretchable film is formed using the compound having a (meth)acrylate group at a terminal, the curing can be performed by combining heat-curing and photo-curing. For example, it is possible to form a stretchable film, which serves as base, by heat-curing, and then form a stretchable film having a uneven pattern on the base by photo-curing. The merits of photo-curing are that heating is not necessarily essential, and the curing can be performed in a short period. The demerit is that the area where light does not reach cannot be cured. By combining heat-curing and photo-curing, a curing method that takes advantage of each curing merit can be selected.

When the compound having a (meth)acrylate group at a terminal is cured by heating, the heat-curing can be performed, for example, with a hot plate, in an oven, or by irradiation of far infrared ray. The heating conditions are preferably at 30 to 150° C. for 10 seconds to 60 minutes, more preferably at 50 to 120° C. for 30 seconds to 20 minutes. The baking environment may be in the atmosphere, in an inert gas, or in vacuum.

When the compound having a (meth)acrylate group at a terminal is cured by light irradiation, the curing by light irradiation is preferably performed with light having a wavelength of 200 to 500 nm. As the light source, for example, a halogen lamp, a xenon lamp, excimer laser, a metal halide lamp, LED, or the like can be used. Alternatively, electron beam irradiation may be adopted. The irradiation quantity is preferably in a range of 1 mJ/cm$^2$ to 100 J/cm$^2$.

The stretchable film having a repeated uneven pattern on the top surface adopted in the present invention can be used not only as a self-standing film alone, but can also be formed on fiber or a membrane film.

<Use Examples of the Inventive Stretchable Wiring Film>

Here, FIGS. 3 and 9 to 14 show examples of using the inventive stretchable wiring film. FIG. 3 is a schematic illustration of an electrocardiograph 1 formed on the stretchable film 6, which is viewed from a bio-electrode side. As shown in FIG. 3, in the electrocardiograph 1, three bio-electrodes 2 are linked with each other by a wiring 3, which conducts electric signals, and are connected to a center device 4; and adhesive parts 5 are disposed around the bio-electrodes 2. The electrocardiograph 1 is described in Patent Document 1. Here, the inventive stretchable wiring film is a combination of the stretchable film 6 and the wiring 3 (stretchable wiring). Moreover, FIG. 9 is a cross-sectional view showing a state where the stretchable film 6 having a uneven pattern portion 6-1 is provided on the substrate 7. FIG. 10 is a cross-sectional view showing a state where the electrocardiograph 1 is formed on the stretchable film 6. FIG. 11 is a cross-sectional view showing a state where the stretchable wiring 3 and the center device 4 of the electrocardiograph 1 are covered with the stretchable film 6.

As the material of the wiring 3, electrically conductive materials are generally used, including carbon and metals such as gold, silver, platinum, copper, tin, titanium, nickel, aluminum, tungsten, molybdenum, ruthenium, chromium, indium, and stainless steel. By applying the electro-conductive material onto the uneven substrate, a wire having a meandering-shaped structure is formed in a vertical direction of the film. Thereby, the decrease in electric conductivity in stretching can be suppressed to the minimum. Since the meandering-shaped structure is formed in the depth direction of the film, when the meandering-shaped structure is observed from the top of the film, the structure is just seen as a straight flat wire. This provides excellent design, too.

Since the electrocardiograph 1 has to be attached to skin, the adhesive part 5 is disposed around each of the bio-electrodes 2 in FIGS. 10, 11 in order not to separate the bio-electrode 2 from the skin. Incidentally, when the bio-electrode 2 has adhesiveness, the surrounding adhesive part 5 is not necessarily essential.

This electrocardiograph 1 is formed on the stretchable film 6, which is the inventive stretchable film having an uneven top surface, as shown in FIG. 3. Since the stretchable film 6 has little stickiness on its top surface, when printing is performed thereon by screen printing and so on, the stretchable film 6 shows favorable printing plate-release. If the printing plate-release is unfavorable, the paste is released together when the printing plate is released. This is not preferable because the paste may not be transferred on the stretchable film properly.

Further, the stretchable wiring 3 can be covered with the stretchable film 6. In this case, the stretchable film 6 does not necessarily have to have the uneven top surface.

Furthermore, it is also possible to form a stretchable film as shown in FIG. 12 by inverting the stretchable film shown in FIG. 9, and forming an uneven film on the other surface, so that uneven patterns are formed on both sides (top surface and bottom surface) of the stretchable film. Cross-sectional views of an electrocardiograph using this stretchable film are shown in FIG. 13 and FIG. 14.

The inventive method for forming a stretchable wiring film as described above makes it possible to easily form a stretchable wiring film which has less decrease in electric conductivity in stretching, and in which a stretchable wiring is formed on a stretchable film having excellent stretchability and strength equivalent or superior to those of polyurethane, the stretchable film also having high water repellency and low tackiness on the film top surface.

EXAMPLE

Hereinafter, the present invention will be specifically described with reference to Examples and Comparative Examples. However, the present invention is not limited thereto. Incidentally, the weight average molecular weight (Mw) represents a weight average molecular weight in terms of polystyrene determined by gel permeation chromatography (GPC).

Silicone pendant urethane (meth)acrylates 1 to 13 and Urethane (meth)acrylates 1 to 3, which were blended as the compound having a (meth)acrylate group at a terminal to Stretchable film materials 1 to 18 shown in Table 1, are shown below.

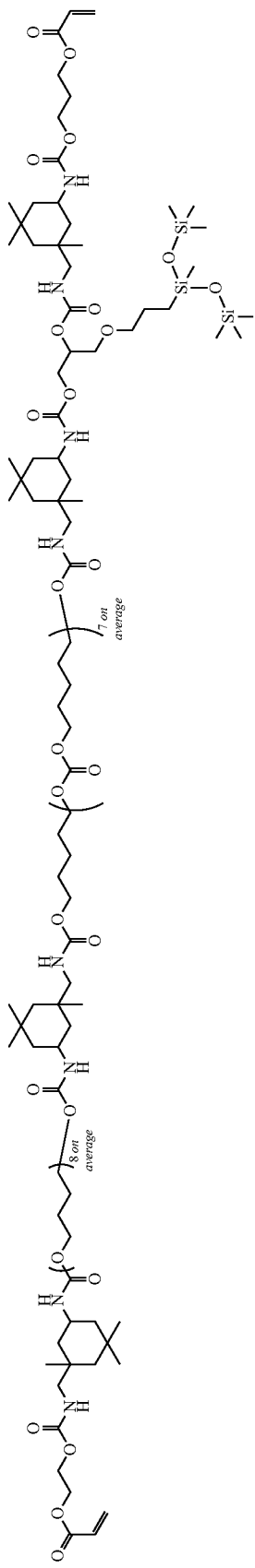
Silicone pendant urethane (meth) acrylate 1
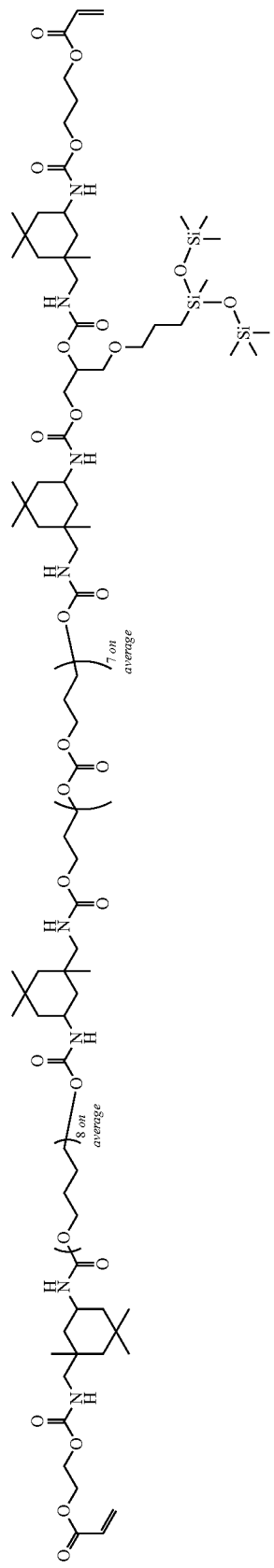
Silicone pendant urethane (meth) acrylate 2

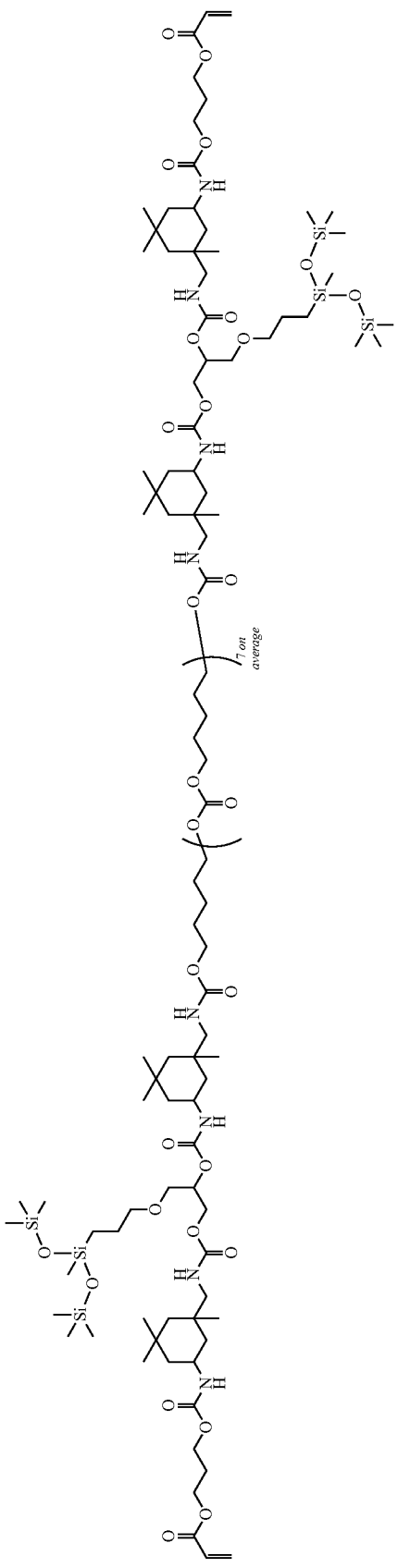
Silicone pendant urethane (meth) acrylate 3
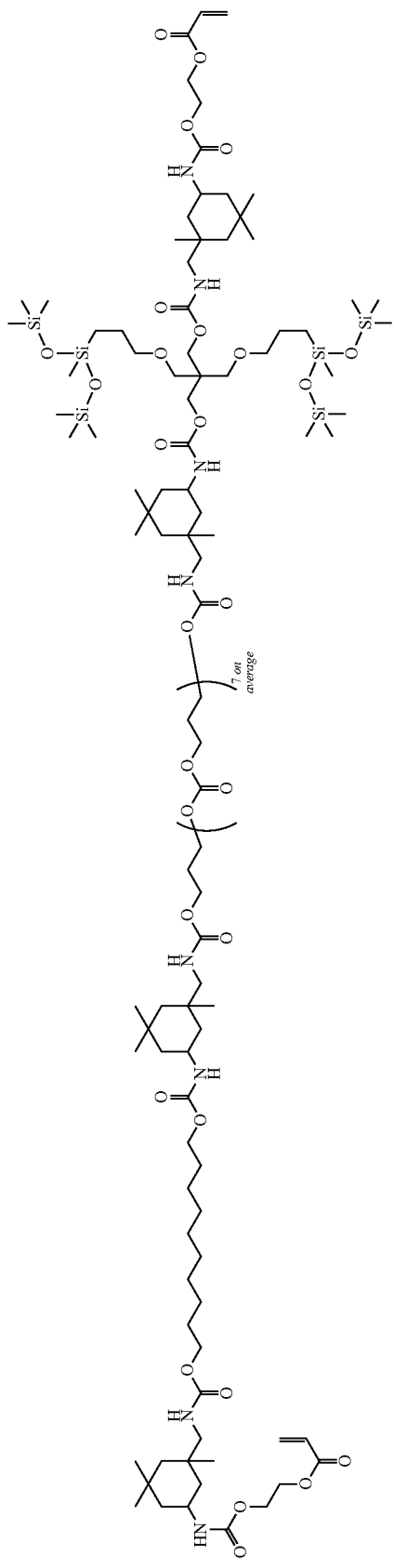
Silicone pendant urethane (meth) acrylate 4

-continued
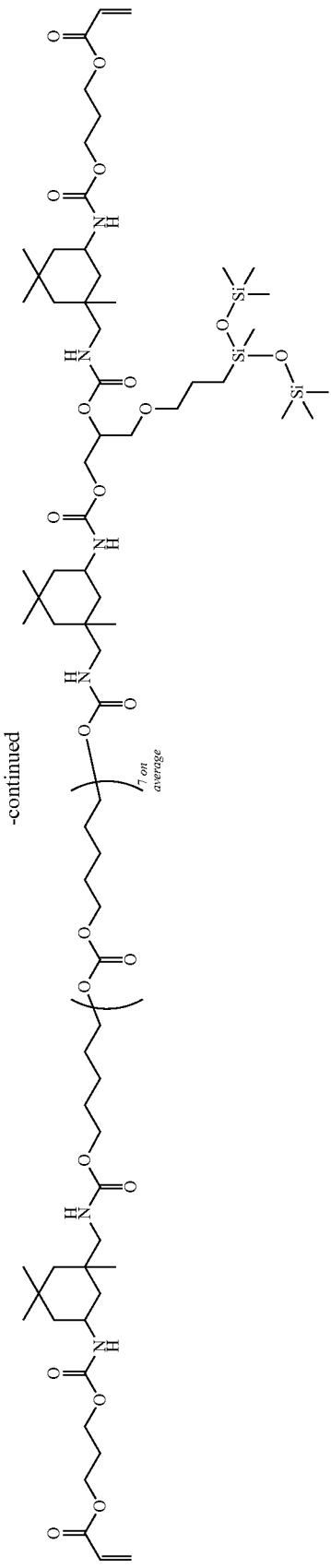
Silicone pendant urethane (meth) acrylate 5
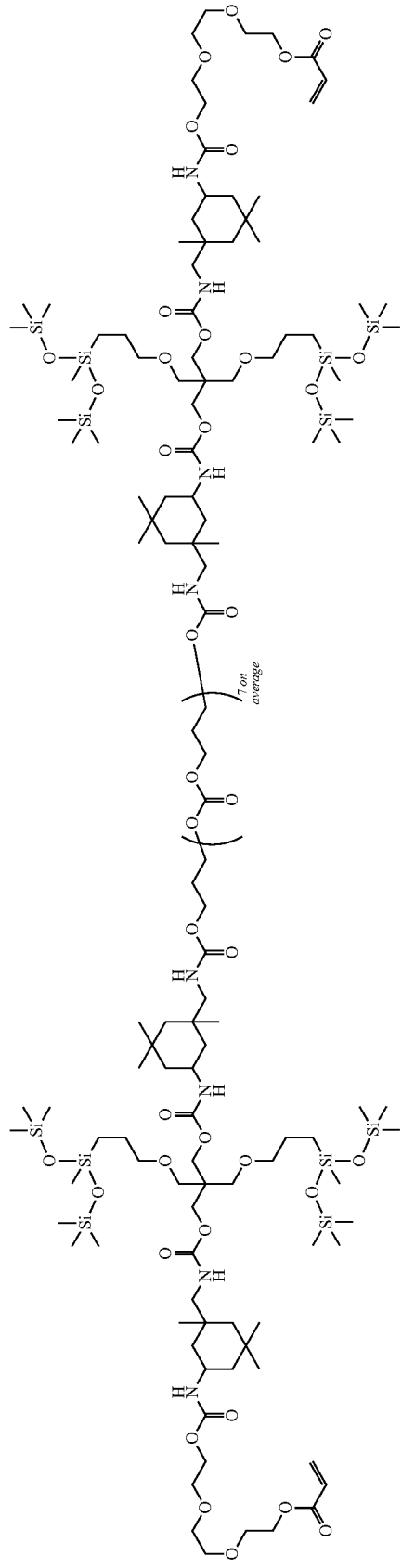
Silicone pendant urethane (meth) acrylate 6

-continued
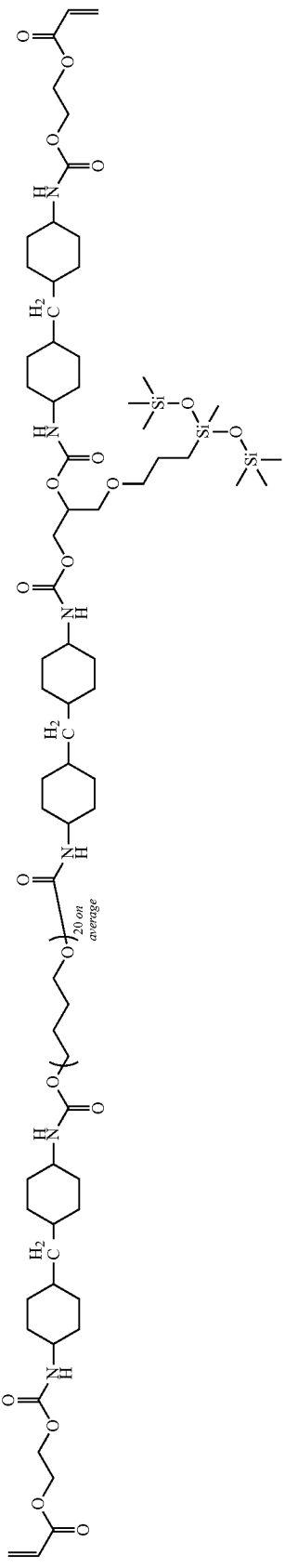
Silicone pendant urethane (meth) acrylate 7
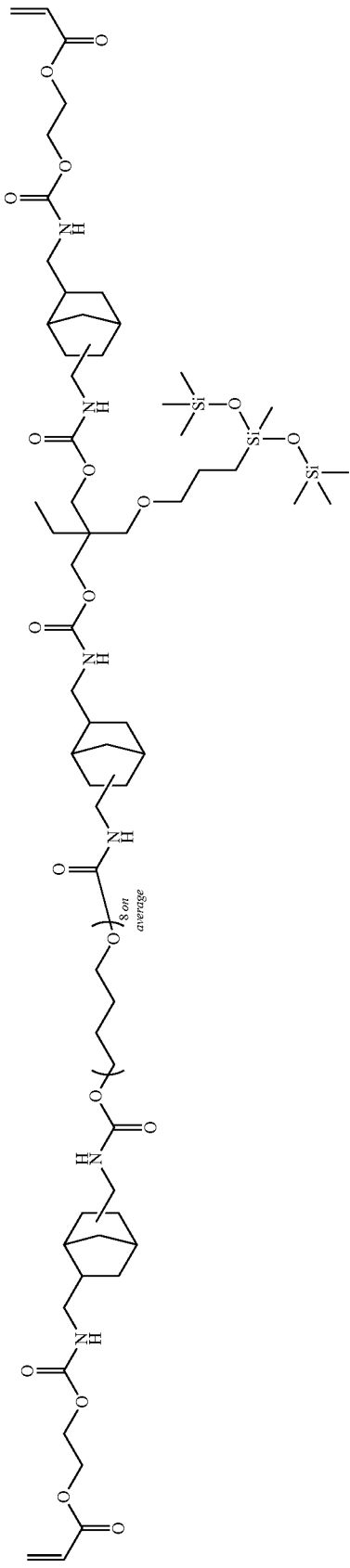
Silicone pendant urethane (meth) acrylate 8

-continued
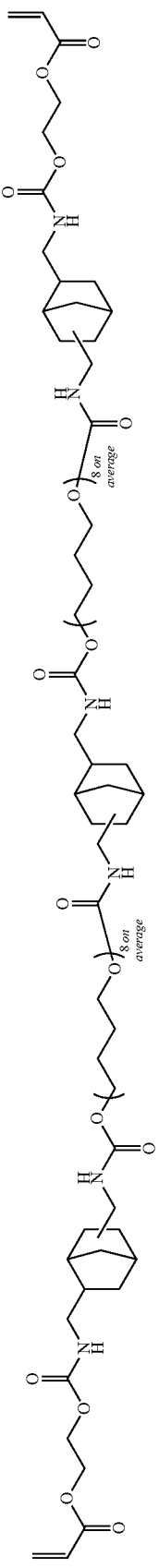
Urethane (meth) acrylate 1
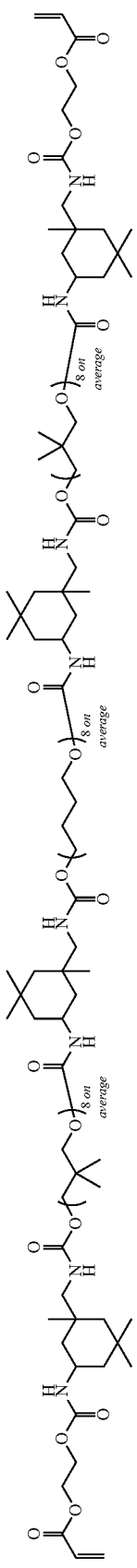
Urethane (meth) acrylate 2
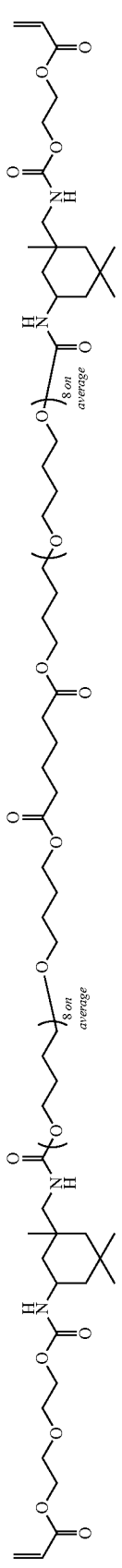
Urethane (meth) acrylate 3

-continued
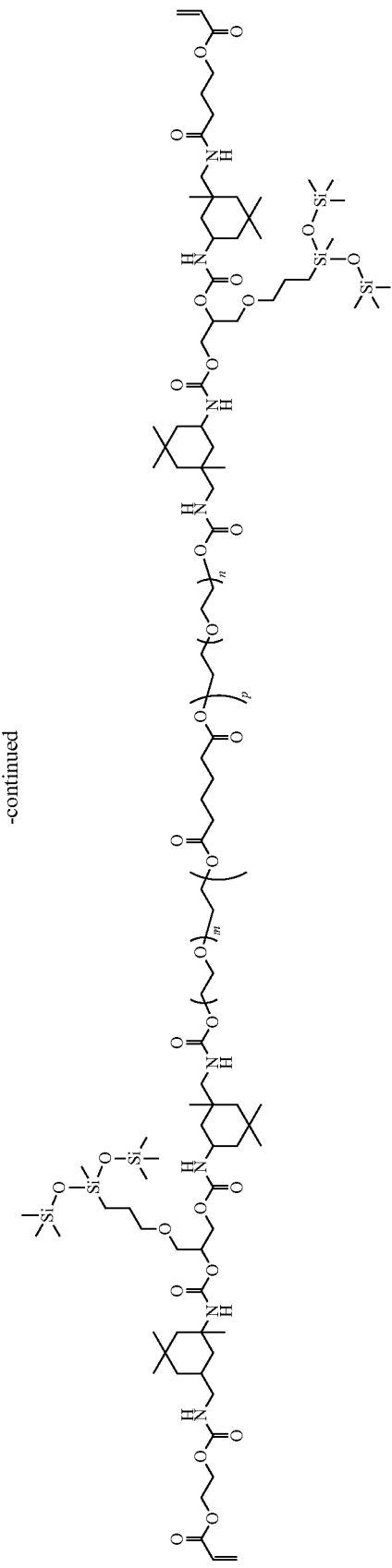
Silicone pendant urethane (meth) acrylate 9
m + n = 20
p = 10
on average
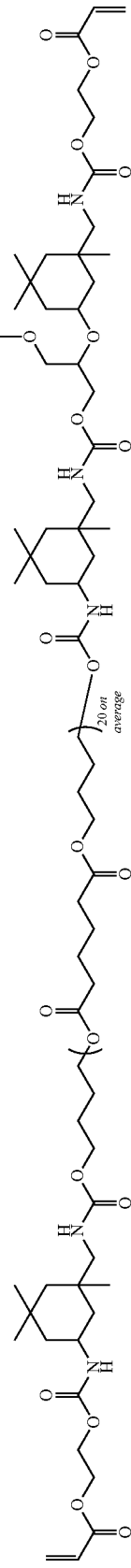
Silicone pendant urethane (meth) acrylate 10

-continued
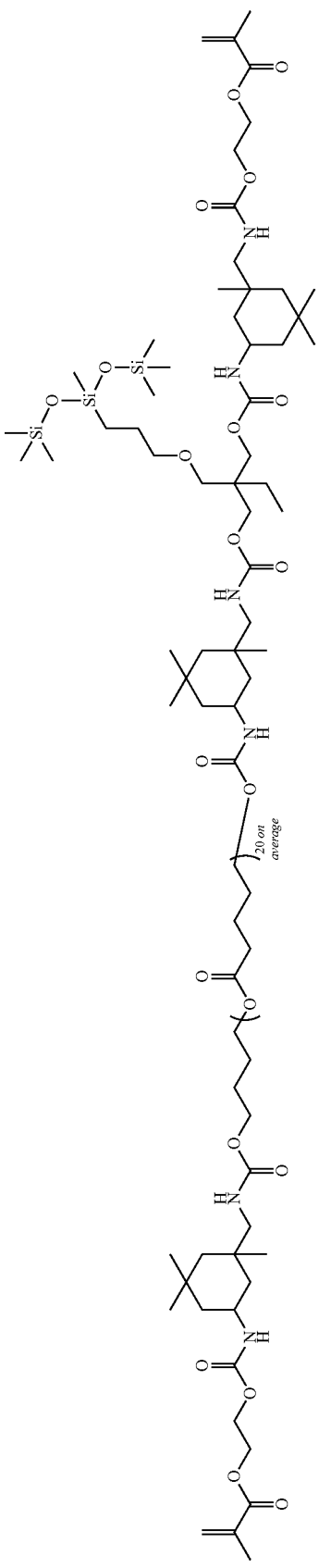
Silicone pendant urethane (meth) acrylate 11
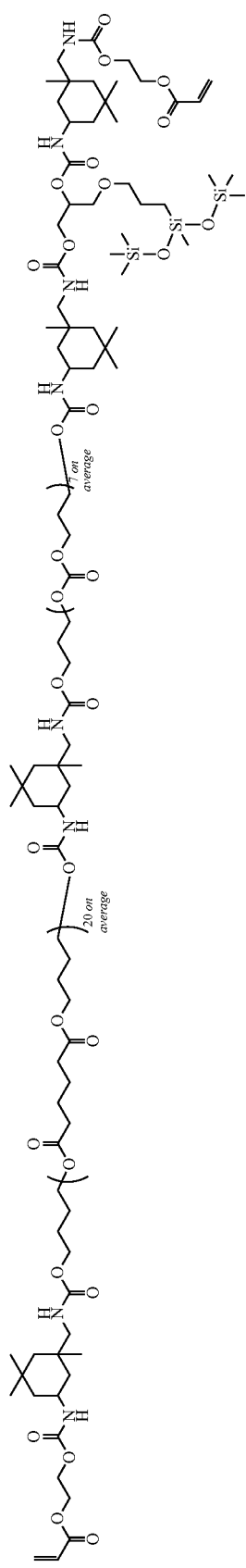
Silicone pendant urethane (meth) acrylate 12
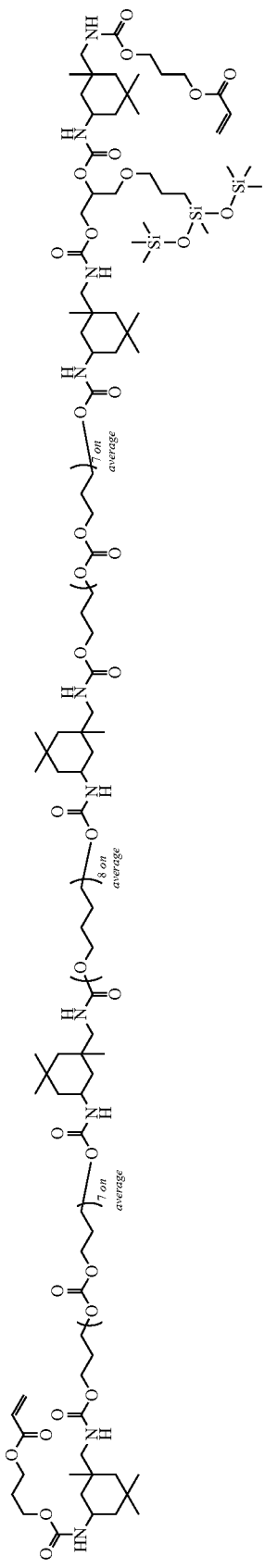
Silicone pendant urethane (meth) acrylate 13

Photo radical generator-1 blended as an additive to Stretchable film materials 1 to 18 is shown below. Photo radical generator-1: diphenyl(2,4,6-trimethylbenzoyl)phosphine oxide A monomer having an alkyl group or an aryl group blended to Stretchable film materials 1 to 18 is shown below.

Monomer having an alkyl group or an aryl group: isobornyl acrylate or trimethylolpropane triacrylate Examples, Comparative Examples According to compositions shown in Table 1, Stretchable film materials 1 to 18 (compositions for forming a stretchable film) were prepared by mixing the silicone urethane compounds having a (meth)acrylate group at a terminal, and so forth, with the photo radical generator.

According to a composition shown in Table 2, a stretchable electro-conductive paste (Stretchable electro-conductive paste material 1) was prepared by mixing a styrene-butadiene rubber manufactured by Sigma-Aldrich Inc. with an organic solvent and silver flakes manufactured by Sigma-Aldrich Inc.

TABLE 1

| Stretchable film material | Urethane acrylate (parts by mass) | Additive (parts by mass) |
|---|---|---|
| Stretchable film material 1 | Silicone pendant urethane (meth)acrylate 1 (70) Isobornyl acrylate (30) | Photo radical generator-1 (1) |
| Stretchable film material 2 | Silicone pendant urethane (meth)acrylate 2 (70) Isobornyl acrylate (30) | Photo radical generator-1 (1) |
| Stretchable film material 3 | Silicone pendant urethane (meth)acrylate 3 (75) Isobornyl acrylate (25) | Photo radical generator-1 (1) |
| Stretchable film material 4 | Silicone pendant urethane (meth)acrylate 4 (70) Isobornyl acrylate (30) | Photo radical generator-1 (1) |
| Stretchable film material 5 | Silicone pendant urethane (meth)acrylate 5 (80) Isobornyl acrylate (20) | Photo radical generator-1 (1) |
| Stretchable film material 6 | Silicone pendant urethane (meth)acrylate 6 (80) Isobornyl acrylate (20) | Photo radical generator-1 (1) |
| Stretchable film material 7 | Silicone pendant urethane (meth)acrylate 1 (70) Isobornyl acrylate (27) Trimethylolpropane triacrylate (3) | Photo radical generator-1 (1) |
| Stretchable film material 8 | Silicone pendant urethane (meth)acrylate 7 (70) Isobornyl acrylate (30) | Photo radical generator-1 (1) |
| Stretchable film material 9 | Silicone pendant urethane (meth)acrylate 8 (70) Isobornyl acrylate (30) | Photo radical generator-1 (1) |
| Stretchable film material 10 | Urethane (meth)acrylate 1 (70) Isobornyl acrylate (30) | Photo radical generator-1 (1) |
| Stretchable film material 11 | Urethane (meth)acrylate 2 (100) Isobornyl acrylate (30) | Photo radical generator-1 (1) |
| Stretchable film material 12 | Urethane (meth)acrylate 3 (70) Isobornyl acrylate (30) | Photo radical generator-1 (1) |
| Stretchable film material 13 | Silicone pendant urethane (meth)acrylate 1 (40) Silicone pendant urethane (meth)acrylate 7 (30) Isobornyl acrylate (30) | Photo radical generator-1 (1) |
| Stretchable film material 14 | Silicone pendant urethane (meth)acrylate 9 (75) Isobornyl acrylate (25) | Photo radical generator-1 (1) |
| Stretchable film material 15 | Silicone pendant urethane (meth)acrylate 10 (75) Isobornyl acrylate (25) | Photo radical generator-1 (1) |
| Stretchable film material 16 | Silicone pendant urethane (meth)acrylate 11 (70) Isobornyl acrylate (30) | Photo radical generator-1 (1) |
| Stretchable film material 17 | Silicone pendant urethane (meth)acrylate 12 (75) Isobornyl acrylate (25) | Photo radical generator-1 (1) |
| Stretchable film material 18 | Silicone pendant urethane (meth)acrylate 13 (70) Isobornyl acrylate (30) | Photo radical generator-1 (1) |

TABLE 2

| Stretchable electro-conductive paste | Resin (parts by mass) | Additive (parts by mass) | Organic solvent (parts by mass) |
|---|---|---|---|
| Stretchable electro-conductive paste material 1 | styrene-butadiene rubber (10) | silver flakes (40) | dimethyl succinate (40) |

(Preparation of Stretchable Films)

A 6-inch synthetic quartz substrate was prepared whose surface had holes arranged in a lattice form, each hole being formed at an angle of 70° with a depth of 5 micron, one side of 10 micron, and a pitch of 20 micron. This synthetic quartz was prepared by photolithography and dry etching. The substrate was baked on a hot plate at 150° C. for 60 seconds, then spin-coated with a 1% toluene solution of triethoxy (1H,1H,2H,2H-heptadecafluorodecyl)silane, and baked on a hot plate at 100° C. for 60 seconds to evaporate the solvent. Consequently, the quartz substrate was fluoroalkylated.

In Example 1 and Comparative Example 3, the stretchable film materials shown in Table 3 as the uneven pattern film material were applied using a slit coater, and cured by irradiation with light of 500 mJ/cm$^2$ from a 1,000 W xenon lamp in a nitrogen atmosphere. The resultant was peeled from the synthetic quartz substrate. Thus, stretchable films each having the uneven pattern on the top surface were prepared.

In Examples 2 to 8 and 10 to 15, the stretchable film materials shown in Table 3 as the flat-film material were each applied using a slit coater onto a Teflon(registered trademark) film, and cured by irradiation with light of 500 mJ/cm$^2$ from a 1,000 W xenon lamp in a nitrogen atmosphere to form a flat stretchable film. The stretchable film materials shown in Table 3 as the uneven pattern film material were each applied by the bar coating method onto the fluoroalkylated quartz substrate. Then, the flat stretchable film prepared above was firmly attached to the resulting surface. The uneven portion at the top surface of the stretchable film was cured by irradiation with light of 500 mJ/cm$^2$ from a 1,000 W xenon lamp in a nitrogen atmosphere, and peeled from the synthetic quartz substrate. Thus, stretchable films each having the uneven pattern on the top surface were formed.

In Example 9, the stretchable film material in Table 3 as the uneven pattern film material was applied by the bar coating method onto the fluoroalkylated quartz substrate. The uneven portion at the top surface of the stretchable film was cured by irradiation with light of 500 mJ/cm$^2$ from a 1,000 W xenon lamp in a nitrogen atmosphere. Then, the stretchable film material shown in Table 3 as the flat-film material was applied using a slit coater onto the resulting surface, irradiated with light of 500 mJ/cm² from a 1,000 W xenon lamp in a nitrogen atmosphere, and peeled from the uneven quartz substrate. Thus, a stretchable film having the uneven pattern on the top surface was prepared.

In Comparative Examples 1, 2, the stretchable film materials shown in Table 3 as the flat-film material were each applied using a slit coater onto a Teflon(registered trademark) film. The stretchable film was cured by irradiation with light of 500 mJ/cm² from a 1,000 W xenon lamp in a nitrogen atmosphere.

(Measurement of Film Thickness, Contact Angle, Stretching Property, and Strength)

After the curing, the stretchable films having a repeated uneven pattern on the top surface (Examples 1 to 15) and the stretchable films of Comparative Examples (Comparative Examples 1 to 3) were measured for film thickness and contact angle with water on the top surface. Moreover, after each stretchable film was measured for the contact angle with water on the top surface, the stretchable film was peeled from the substrate to measure the stretching property and strength by a method in conformity to JIS K 6251. Then, using a stencil mask having a thickness of 50 micron, an opening width of 1 mm and length of 50 mm, the electro-conductive paste was applied onto the stretchable film (stretchable substrate), and baked at 120° C. for 30 minutes to evaporate the solvent. Thus, a stretchable wiring was formed. The electric resistance at each end portion of the stretchable wiring was measured when stretched by 0% and 20%. Table 3 shows the results.

TABLE 3

| | Uneven pattern film material | Flat-film material | Stretchable film thickness (μm) | Contact angle (°) | Elongation (%) | Strength (MPa) | Stretchable electro-conductive paste | Resistance (Ω) when stretched by 0% | Resistance (Ω) when stretched by 20% |
|---|---|---|---|---|---|---|---|---|---|
| Example 1 | Stretchable film material 1 | — | 180 | 120 | 290 | 16.1 | Stretchable electro-conductive paste 1 | 28 | 85 |
| Example 2 | Stretchable film material 2 | Stretchable film material 7 | 190 | 122 | 280 | 15.1 | Stretchable electro-conductive paste 1 | 21 | 76 |
| Example 3 | Stretchable film material 3 | Stretchable film material 8 | 210 | 120 | 290 | 16.3 | Stretchable electro-conductive paste 1 | 29 | 75 |
| Example 4 | Stretchable film material 4 | Stretchable film material 9 | 226 | 128 | 280 | 14.3 | Stretchable electro-conductive paste 1 | 38 | 55 |
| Example 5 | Stretchable film material 5 | Stretchable film material 10 | 160 | 118 | 290 | 16.0 | Stretchable electro-conductive paste 1 | 28 | 48 |
| Example 6 | Stretchable film material 6 | Stretchable film material 10 | 230 | 128 | 290 | 14.5 | Stretchable electro-conductive paste 1 | 18 | 36 |
| Example 7 | Stretchable film material 6 | Stretchable film material 11 | 250 | 128 | 310 | 15.3 | Stretchable electro-conductive paste 1 | 43 | 85 |
| Example 8 | Stretchable film material 6 | Stretchable film material 12 | 210 | 129 | 320 | 15.8 | Stretchable electro-conductive paste 1 | 41 | 82 |
| Example 9 | Stretchable film material 6 | Stretchable film material 12 | 260 | 130 | 290 | 15.0 | Stretchable electro-conductive paste 1 | 48 | 81 |
| Example 10 | Stretchable film material 13 | Stretchable film material 7 | 230 | 122 | 280 | 16.1 | Stretchable electro-conductive paste 1 | 23 | 71 |
| Example 11 | Stretchable film material 14 | Stretchable film material 7 | 210 | 210 | 290 | 17.3 | Stretchable electro-conductive paste 1 | 29 | 77 |
| Example 12 | Stretchable film material 15 | Stretchable film material 7 | 226 | 198 | 310 | 17.3 | Stretchable electro-conductive paste 1 | 42 | 59 |
| Example 13 | Stretchable film material 16 | Stretchable film material 7 | 160 | 174 | 340 | 19.0 | Stretchable electro-conductive paste 1 | 22 | 44 |

TABLE 3-continued

| | Uneven pattern film material | Flat-film material | Stretchable film thickness (μm) | Contact angle (°) | Elongation (%) | Strength (MPa) | Stretchable electro-conductive paste | Resistance (Ω) when stretched by 0% | Resistance (Ω) when stretched by 20% |
|---|---|---|---|---|---|---|---|---|---|
| Example 14 | Stretchable film material 17 | Stretchable film material 7 | 230 | 166 | 320 | 22.5 | Stretchable electro-conductive paste 1 | 28 | 38 |
| Example 15 | Stretchable film material 18 | Stretchable film material 7 | 250 | 149 | 350 | 21.3 | Stretchable electro-conductive paste 1 | 41 | 55 |
| Comparative Example 1 | — | Stretchable film material 1 | 180 | 96 | 340 | 13.2 | Stretchable electro-conductive paste 1 | 35 | 354 |
| Comparative Example 2 | — | Stretchable film material 10 | 220 | 72 | 430 | 16.1 | Stretchable electro-conductive paste 1 | 30 | 620 |
| Comparative Example 3 | Stretchable film material 10 | — | 220 | 58 | 410 | 15.6 | Stretchable electro-conductive paste 1 | 32 | 83 |

As shown in Table 3, in the inventive stretchable wiring film, the stretchable substrate showed higher water repellency, strength, and stretchability; and the stretchable electro-conductive wire formed thereon had such a property that the electric conductivity was less decreased when stretched.

On the other hand, regarding the film with no unevenness on the top surface as in Comparative Examples 1, 2, the electric conductivity was greatly decreased when the film was stretched. When urethane containing no silicon was used as in Comparative Example 3, the water repellency was low.

The above results revealed that the inventive stretchable wiring film has less decrease in electric conductivity in stretching, excellent stretchability and strength, excellent water repellency on the film top surface, and thus excellent properties for use in wearable devices and so on.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A stretchable wiring film comprising:
(A) a stretchable film comprising, at least as a top surface of the stretchable film, a cured product of a stretchable film material comprising a silicone polyurethane resin, wherein the top surface of the stretchable film has a pattern formed with depths of 0.1 μm to 5 mm and pitches of 0.1 μm to 10 mm; and
(B) a stretchable wiring, wherein
the stretchable wiring is formed on the top surface of the stretchable film where the pattern is formed,
wherein the silicone polyurethane resin is a silicone-pendant polyurethane resin having a structure shown by the following general formula (1):

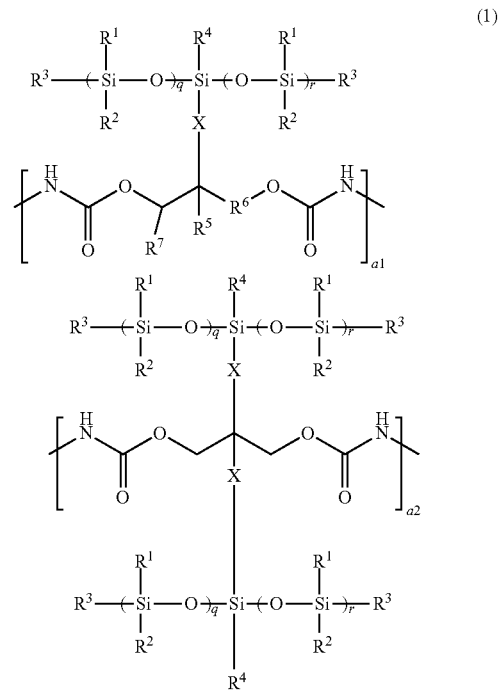

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a $-(OSiR^1R^2)_s-OSiR^1R^2R^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2≤1.0.

2. The stretchable wiring film according to claim 1, wherein the stretchable wiring contains an electro-conductive powder made of carbon or a metal selected from gold, silver, platinum, copper, tin, titanium, nickel, aluminum, tungsten, molybdenum, ruthenium, chromium, and indium.

3. The stretchable wiring film according to claim 1, wherein the silicone-pendant polyurethane resin has a structure shown by the following general formula (2):

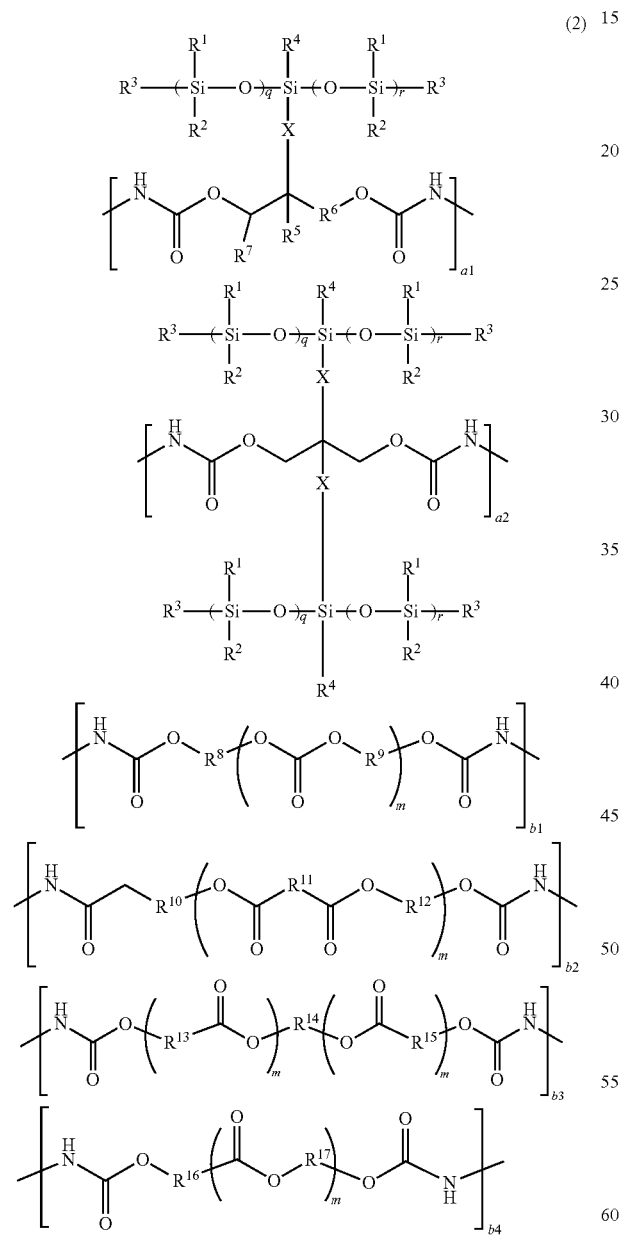

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a —$(OSiR^1R^2)_s$—$OSiR^1R^2R^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2≤1.0; $R^8$ to $R^{17}$ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of 0≤b1<1.0, 0≤b2<1.0, 0≤b3<1.0, 0≤b4<1.0, and 0<b1+b2+b3+b4<1.0.

4. The stretchable wiring film according to claim 2, wherein the silicone-pendant polyurethane resin has a structure shown by the following general formula (2):

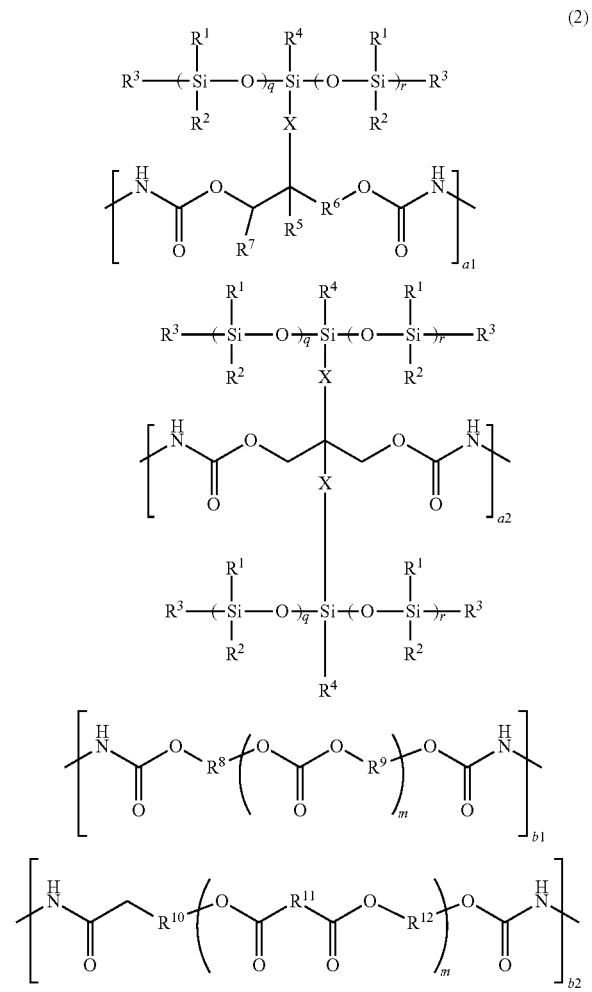

-continued

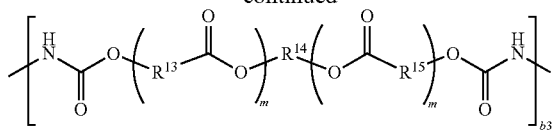

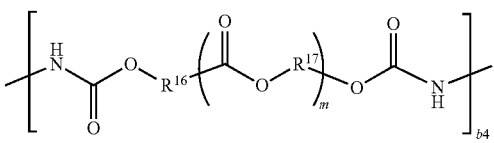

wherein R¹, R², and R³ may be identical to or different from each other and each represent a linear, branched, or cyclic alkyl group having 1 to 6 carbon atoms, a phenyl group, or a 3,3,3-trifluoropropyl group; R⁴'s may be identical to or different from each other and each represent a linear, branched, or cyclic alkyl group having 1 to 6 carbon atoms, a phenyl group, a 3,3,3-trifluoropropyl group, or a —(OSiR¹R²)$_s$—OSiR¹R²R³ group; R⁵ represents a hydrogen atom or a linear or branched alkyl group having 1 to 4 carbon atoms; R⁶ represents a single bond, a methylene group, or an ethylene group; R⁷ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2<1.0; R⁸ to R¹⁷ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of 0≤b1<1.0, 0≤b2<1.0, 0≤b3<1.0, 0≤b4<1.0, and 0<b1+b2+b3+b4<1.0.

5. The stretchable wiring film according to claim 3, wherein the silicone-pendant polyurethane resin has a structure shown by the following general formula (3):

(3)

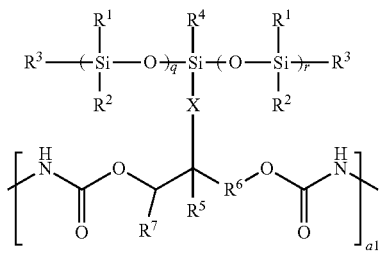

-continued

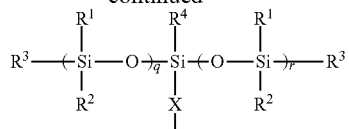

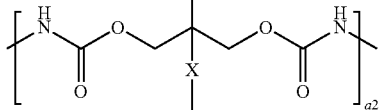

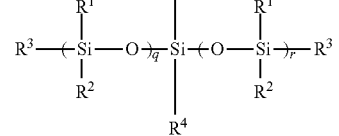

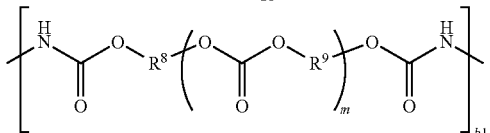

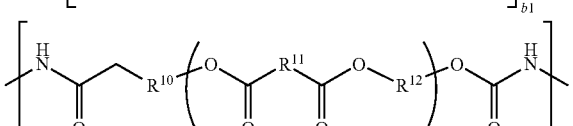

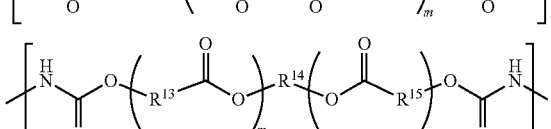

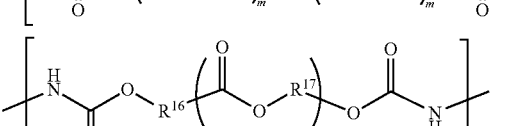

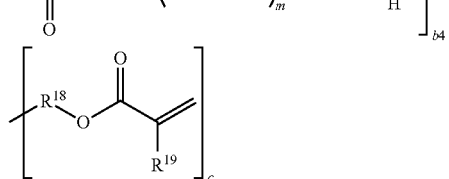

wherein R¹, R², and R³ may be identical to or different from each other and each represent a linear, branched, or cyclic alkyl group having 1 to 6 carbon atoms, a phenyl group, or a 3,3,3-trifluoropropyl group; R⁴'s may be identical to or different from each other and each represent a linear, branched, or cyclic alkyl group having 1 to 6 carbon atoms, a phenyl group, a 3,3,3-trifluoropropyl group, or a —(OSiR¹R²)$_s$—OSiR¹R²R³ group; R⁵ represents a hydrogen atom or a linear or branched alkyl group having 1 to 4 carbon atoms; R⁶ represents a single bond, a methylene group, or an ethylene group; R⁷ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of 0≤a1<1.0, 0≤a2<1.0, and 0<a1+a2<1.0; R⁸ to R¹⁷ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of $0 \leq b1 < 1.0$, $0 \leq b2 < 1.0$, $0 \leq b3 < 1.0$, $0 \leq b4 < 1.0$, and $0 < b1+b2+b3+b4 < 1.0$; $R^{18}$ represents a linear, branched, or cyclic alkylene group having 1 to 20 carbon atoms and optionally having an ether group or an ester group; $R^{19}$ represents a hydrogen atom or a methyl group; and "c" represents the number of unit in one molecule and satisfies a range of $1 \leq c \leq 4$.

6. The stretchable wiring film according to claim 4, wherein the silicone-pendant polyurethane resin has a structure shown by the following general formula (3):

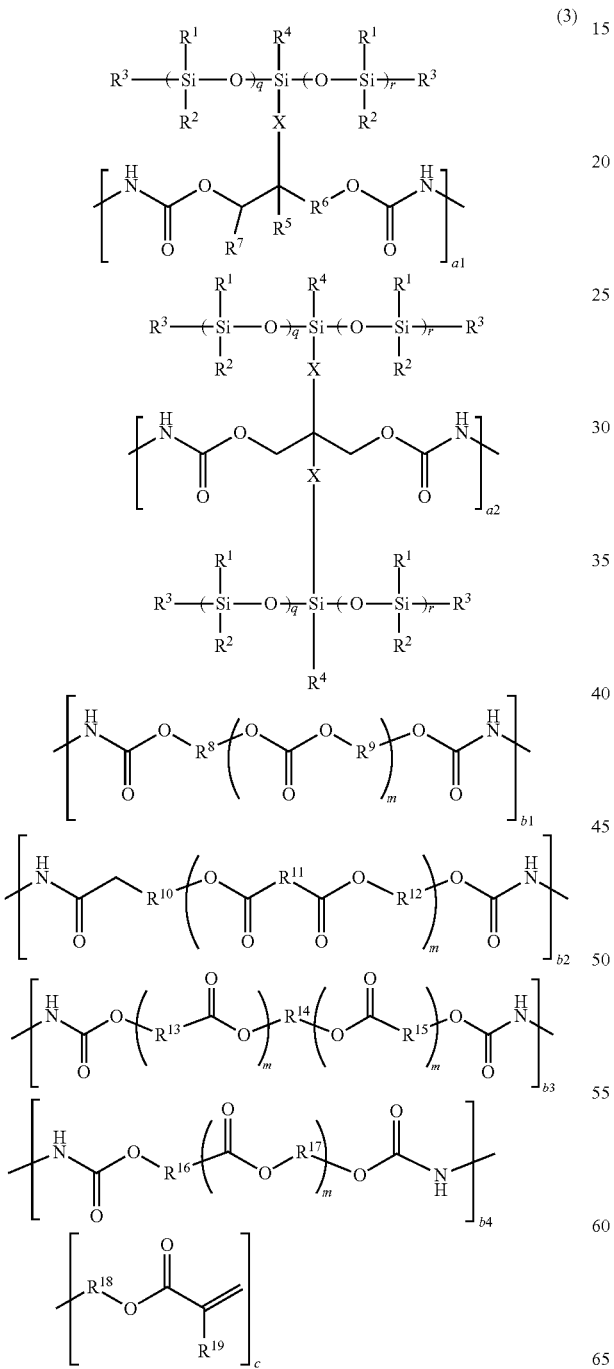

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a $-(OSiR^1R^2)_s-OSiR^1R^2R^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of $0 \leq a1 < 1.0$, $0 \leq a2 < 1.0$, and $0 < a1+a2 < 1.0$; $R^8$ to $R^{17}$ may be identical to or different from each other and each represent a linear, branched, or cyclic alkylene group having 2 to 12 carbon atoms, or an arylene group having 6 to 12 carbon atoms; "m"s may be identical to or different from each other and each represent 1 to 200; and b1, b2, b3, and b4 represent proportions of repeating units and satisfy ranges of $0 \leq b1 < 1.0$, $0 \leq b2 < 1.0$, $0 \leq b3 < 1.0$, $0 \leq b4 < 1.0$, and $0 < b1+b2+b3+b4 < 1.0$; $R^{18}$ represents a linear, branched, or cyclic alkylene group having 1 to 20 carbon atoms and optionally having an ether group or an ester group; $R^{19}$ represents a hydrogen atom or a methyl group; and "c" represents the number of unit in one molecule and satisfies a range of $1 \leq c \leq 4$.

7. The stretchable wiring film according to claim 1, wherein the stretchable wiring film has an elongation percentage in a range of 5 to 500% in a tensile test stipulated according to JIS K 6251.

8. The stretchable wiring film according to claim 2, wherein the stretchable wiring film has an elongation percentage in a range of 5 to 500% in a tensile test stipulated according to JIS K 6251.

9. The stretchable wiring film according to claim 1, wherein the stretchable wiring film comprises a stretchable film configured to cover a stretchable wiring.

10. The stretchable wiring film according to claim 2, wherein the stretchable wiring film comprises a stretchable film configured to cover a stretchable wiring.

11. The stretchable wiring film according to claim 9, wherein the stretchable film configured to cover a stretchable wiring is a cured product of a stretchable film material comprising the silicone-pendant polyurethane resin having a structure shown by the general formula (1).

12. The stretchable wiring film according to claim 10, wherein the stretchable film configured to cover a stretchable wiring is a cured product of a stretchable film material comprising the silicone-pendant polyurethane resin having a structure shown by the general formula (1).

13. A method for forming a stretchable wiring film, comprising the steps of:
(1) applying a stretchable film material comprising a silicone-pendant polyurethane resin having a structure shown by the following general formula (1) onto a substrate having a pattern formed with depths of 0.1 μm to 5 mm and pitches of 0.1 μm to 10 mm;
(2) curing the stretchable film material by heating and/or light irradiation;

(3) peeling a cured product of the stretchable film material from the substrate to form a stretchable film having a top surface with the pattern; and (4) applying a stretchable electro-conductive paste onto the top surface of the stretchable film where the pattern is formed to form a stretchable wiring,

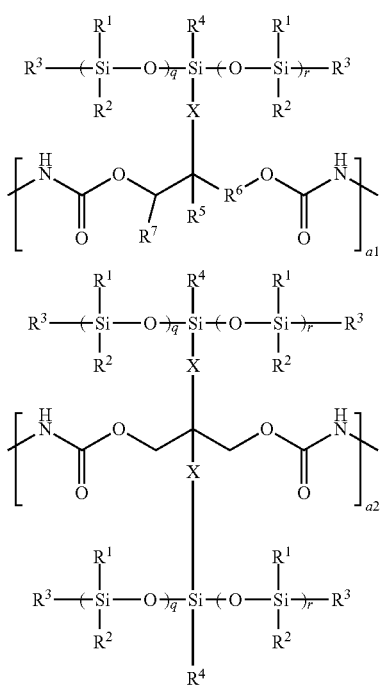

wherein $R^1$, $R^2$, and $R^3$ may be identical to or different from each other and each represent a linear, branched, or cyclic alkyl group having 1 to 6 carbon atoms, a phenyl group, or a 3,3,3-trifluoropropyl group; $R^4$'s may be identical to or different from each other and each represent a linear, branched, or cyclic alkyl group having 1 to 6 carbon atoms, a phenyl group, a 3,3,3-trifluoropropyl group, or a —$(OSiR^1R^2)_s$—$OSiR^1R^2R^3$ group; $R^5$ represents a hydrogen atom or a linear or branched alkyl group having 1 to 4 carbon atoms; $R^6$ represents a single bond, a methylene group, or an ethylene group; $R^7$ represents a hydrogen atom or a methyl group; X represents a linear or branched alkylene group having 3 to 7 carbon atoms and optionally containing an ether group; "q", "r", and "s" each represent an integer in a range of 0 to 20; and a1 and a2 represent proportions of repeating units and satisfy ranges of $0 \leq a1 < 1.0$, $0 \leq a2 < 1.0$, and $0 < a1+a2 \leq 1.0$.

14. The method for forming a stretchable wiring film according to claim 13, comprising, between the step (1) and the step (2), (1') a step of pressure-bonding a polyurethane film onto the stretchable film material.

15. The method for forming a stretchable wiring film according to claim 13, comprising, between the step (2) and the step (3),
(2'-1) a step of coating the cured product of the stretchable film material with a stretchable film material containing a polyurethane resin, and
(2'-2) a step of curing the stretchable film material containing the polyurethane resin by heating and/or light irradiation to form a polyurethane film.

16. The method for forming a stretchable wiring film according to claim 13, wherein the stretchable electro-conductive paste contains an electro-conductive powder made of carbon or a metal selected from gold, silver, platinum, copper, tin, titanium, nickel, aluminum, tungsten, molybdenum, ruthenium, chromium, and indium.

\* \* \* \* \*